United States Patent
Bhadra et al.

(10) Patent No.: US 10,864,373 B2
(45) Date of Patent: Dec. 15, 2020

(54) SYSTEMS FOR TREATMENT OF A NEUROLOGICAL DISORDER USING ELECTRICAL NERVE CONDUCTION BLOCK

(71) Applicant: Case Western Reserve University, Cleveland, OH (US)

(72) Inventors: Niloy Bhadra, Cleveland, OH (US); Narendra Bhadra, Cleveland, OH (US); Kevin L. Kilgore, Cleveland, OH (US); Scott Lempka, Cleveland, OH (US); Jesse Wainright, Cleveland, OH (US); Tina Vrabec, Cleveland, OH (US); Manfred Franke, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 217 days.

(21) Appl. No.: 16/060,979

(22) PCT Filed: Dec. 15, 2016

(86) PCT No.: PCT/US2016/066960
§ 371 (c)(1),
(2) Date: Jun. 11, 2018

(87) PCT Pub. No.: WO2017/106519
PCT Pub. Date: Jun. 22, 2017

(65) Prior Publication Data
US 2018/0361155 A1    Dec. 20, 2018

Related U.S. Application Data

(63) Continuation-in-part of application No. 14/969,826, filed on Dec. 15, 2015, now Pat. No. 9,694,181.

(51) Int. Cl.
*A61N 1/06* (2006.01)
*A61N 1/36* (2006.01)
(Continued)

(52) U.S. Cl.
CPC ........ *A61N 1/36071* (2013.01); *A61N 1/0551* (2013.01); *A61N 1/06* (2013.01);
(Continued)

(58) Field of Classification Search
USPC .......................................... 607/46
See application file for complete search history.

(56) References Cited

U.S. PATENT DOCUMENTS 4,057,069 A   11/1977   Dorffer et al.
4,917,093 A    4/1990   Dufresne et al.
(Continued)

FOREIGN PATENT DOCUMENTS

DE    4324185        1/1995
JP    2006508768 A   3/2006
(Continued)

OTHER PUBLICATIONS

PCT International Search Report and Written Opinion for corresponding International Application Serial No. PCT/US2016/066960, dated Mar. 10, 2017, pp. 1-12.
(Continued)

*Primary Examiner* — Nicole F Lavert
(74) *Attorney, Agent, or Firm* — Tarolli, Sundheim, Covell & Tummino LLP

(57) ABSTRACT

One aspect of the present disclosure is a system including a waveform generator, a controller, and an electrical contact. The waveform generator is for generating an electrical nerve conduction block (ENCB). The controller is coupled with the waveform generator. The controller is configured to receive an input comprising at least one parameter to adjust
(Continued)

the ENCB. The electrical contact is coupled with the waveform generator. The electrical contact is configured to be placed into contact with a nerve. The electrical contact comprises a high charge capacity material that prevents formation of damaging electro-chemical products at a charge delivered by the ENCB. The electrical contact is configured to deliver the ENCB to the nerve to block transmission of a signal related to a pain through the nerve.

11 Claims, 17 Drawing Sheets

(51) Int. Cl.
    *A61N 1/05*     (2006.01)
    *A61N 1/20*     (2006.01)

(52) U.S. Cl.
    CPC ............ *A61N 1/20* (2013.01); *A61N 1/36021* (2013.01); *A61N 1/36057* (2013.01); *A61N 1/36103* (2013.01); *A61N 1/36125* (2013.01); *A61N 1/36171* (2013.01); *A61N 1/36175* (2013.01)

(56) References Cited

U.S. PATENT DOCUMENTS

| | | |
|---|---|---|
| 5,034,589 A | 7/1991 | Evans et al. |
| 5,833,714 A | 11/1998 | Loeb |
| 5,868,743 A | 2/1999 | Saul et al. |
| 6,189,536 B1 | 2/2001 | Martinez et al. |
| 6,192,279 B1 | 2/2001 | Barreras, Sr. et al. |
| 6,205,359 B1 | 3/2001 | Boveja |
| 6,293,266 B1 | 9/2001 | Oetting |
| 6,366,813 B1 | 4/2002 | DiLorenzo |
| 6,600,956 B2 | 7/2003 | Maschino et al. |
| 6,671,561 B1 | 12/2003 | Moaddeb |
| 6,819,956 B2 | 11/2004 | DiLorenzo |
| 6,895,280 B2 | 5/2005 | Meadows et al. |
| 6,907,295 B2 | 6/2005 | Gross et al. |
| 6,937,893 B2 | 8/2005 | Danz et al. |
| 6,974,533 B2 | 12/2005 | Zhou |
| 6,975,907 B2 | 12/2005 | Zanakis et al. |
| 7,079,903 B2 | 7/2006 | O'Brien |
| 7,216,001 B2 | 5/2007 | Hacker et al. |
| 7,421,299 B2 | 9/2008 | Frericks et al. |
| 7,428,438 B2 | 9/2008 | Parramon et al. |
| 7,437,193 B2 | 10/2008 | Parramon et al. |
| 7,502,652 B2 | 3/2009 | Gaunt et al. |
| 7,587,241 B2 | 9/2009 | Parramon et al. |
| 7,638,032 B2 | 12/2009 | Zhou et al. |
| 7,691,252 B2 | 4/2010 | Zhou et al. |
| 7,734,340 B2 | 6/2010 | De Ridder |
| 7,780,833 B2 | 8/2010 | Hawkins et al. |
| 7,881,808 B2 | 2/2011 | Borgaonkar et al. |
| 7,891,085 B1 | 2/2011 | Kuzma et al. |
| 8,019,439 B2 | 9/2011 | Kuzma et al. |
| 8,034,229 B2 | 10/2011 | Zhou et al. |
| 8,135,478 B2 | 3/2012 | Gross |
| 8,260,426 B2 | 9/2012 | Armstrong et al. |
| 8,271,098 B2 | 9/2012 | Swanson et al. |
| 8,359,102 B2 | 1/2013 | Alataris et al. |
| 8,406,886 B2 | 3/2013 | Gaunt et al. |
| 8,417,352 B2 | 4/2013 | Carroll et al. |
| 8,509,903 B2 | 8/2013 | York et al. |
| 8,612,002 B2 | 12/2013 | Faltys et al. |
| 8,644,933 B2 | 2/2014 | Ozawa et al. |
| 8,646,172 B2 | 2/2014 | Kuzma et al. |
| 8,650,747 B2 | 2/2014 | Kuzma et al. |
| 8,712,533 B2 | 4/2014 | Alataris et al. |
| 8,768,472 B2 | 7/2014 | Fang et al. |
| 8,792,988 B2 | 7/2014 | Alataris et al. |
| 8,897,895 B2 | 11/2014 | Mashiach |
| 8,948,881 B2 | 2/2015 | Fisk |
| 8,983,614 B2 | 3/2015 | Kilgore et al. |
| 9,008,780 B2 | 4/2015 | Nudo et al. |
| 9,008,781 B2 | 4/2015 | Ahmed |
| 9,008,800 B2 | 4/2015 | Ackermann, Jr. et al. |
| 9,011,310 B2 | 4/2015 | Ahmed |
| 9,037,248 B2 | 5/2015 | Durand et al. |
| 9,072,886 B2 | 7/2015 | Gaunt et al. |
| 9,119,966 B2 | 9/2015 | Franke et al. |
| 9,205,265 B2 | 12/2015 | Franke |
| 9,283,391 B2 | 3/2016 | Ahmed |
| 9,327,125 B2 | 5/2016 | Alataris et al. |
| 9,333,356 B2 | 5/2016 | Franke et al. |
| 9,333,357 B2 | 5/2016 | Alataris et al. |
| 9,364,661 B2 | 6/2016 | Kilgore et al. |
| 9,370,664 B2 | 6/2016 | Marnfeldt et al. |
| 9,381,350 B2 | 7/2016 | Ahmed |
| 9,384,990 B2 | 7/2016 | Musa |
| 9,387,322 B2 | 7/2016 | Bhadra et al. |
| 9,393,423 B2 | 7/2016 | Parramon et al. |
| 9,403,014 B2 | 8/2016 | Kilgore et al. |
| 9,480,842 B2 | 11/2016 | Alataris et al. |
| 9,492,665 B2 | 11/2016 | Khalil et al. |
| 9,498,621 B2 | 11/2016 | Ackermann et al. |
| 9,572,979 B2 | 2/2017 | Fridman et al. |
| 9,694,181 B2 | 7/2017 | Bhadra et al. |
| 9,707,390 B2 | 7/2017 | Ahmed |
| 9,707,391 B2 | 7/2017 | Ahmed |
| 9,782,593 B2 | 10/2017 | Parramon et al. |
| 9,789,329 B2 | 10/2017 | Ahmed |
| 9,821,157 B2 | 11/2017 | Ahmed et al. |
| 9,844,668 B2 | 12/2017 | Ahmed |
| 9,889,291 B2 | 2/2018 | Bhadra et al. |
| 10,195,434 B2 | 2/2019 | Bhadra et al. |
| 10,272,240 B2 | 4/2019 | Ackermann et al. |
| 10,441,782 B2 | 10/2019 | Bhadra et al. |
| 2002/0015963 A1 | 2/2002 | Keen |
| 2003/0040785 A1 | 2/2003 | Maschino et al. |
| 2004/0181261 A1 | 9/2004 | Manne |
| 2004/0215285 A1 | 10/2004 | Pollock |
| 2005/0075709 A1 | 4/2005 | Brennen et al. |
| 2006/0085048 A1 | 4/2006 | Cory et al. |
| 2006/0095088 A1* | 5/2006 | De Ridder ......... A61N 1/36085 607/48 |
| 2006/0167527 A1 | 7/2006 | Femano et al. |
| 2006/0184211 A1* | 8/2006 | Gaunt ................. A61B 5/0028 607/48 |
| 2006/0265027 A1 | 11/2006 | Vaingast et al. |
| 2007/0027490 A1 | 2/2007 | Ben-Haim et al. |
| 2007/0043400 A1 | 2/2007 | Donders et al. |
| 2007/0060815 A1 | 3/2007 | Martin et al. |
| 2007/0073354 A1 | 3/2007 | Knudson et al. |
| 2007/0083193 A1 | 4/2007 | Werneth et al. |
| 2007/0255319 A1 | 11/2007 | Greenberg et al. |
| 2007/0291522 A1 | 12/2007 | Toba et al. |
| 2008/0208287 A1 | 8/2008 | Palermo et al. |
| 2008/0208300 A1 | 8/2008 | Pasch |
| 2009/0192567 A1* | 7/2009 | Armstrong ......... A61N 1/36082 607/45 |
| 2009/0254148 A1 | 10/2009 | Borgens et al. |
| 2011/0021943 A1 | 1/2011 | Lacour et al. |
| 2011/0077660 A1* | 3/2011 | Janik ................... A61N 1/0553 606/129 |
| 2011/0160798 A1 | 6/2011 | Ackermann, Jr. et al. |
| 2011/0190849 A1* | 8/2011 | Faltys ................ A61N 1/36125 607/50 |
| 2011/0192720 A1 | 8/2011 | Blauw et al. |
| 2011/0221438 A1 | 9/2011 | Goodwill et al. |
| 2012/0016226 A1 | 1/2012 | Gertner |
| 2012/0053510 A1 | 3/2012 | Peters et al. |
| 2013/0035745 A1 | 2/2013 | Ahmed et al. |
| 2013/0053922 A1 | 2/2013 | Ahmed et al. |
| 2013/0238048 A1 | 9/2013 | Almendinger et al. |
| 2013/0238084 A1 | 9/2013 | Bales, Jr. et al. |
| 2013/0274842 A1 | 10/2013 | Gaunt et al. |
| 2014/0031905 A1 | 1/2014 | Irazoqui et al. |
| 2014/0119480 A1 | 5/2014 | Keegan |
| 2014/0324129 A1 | 10/2014 | Franke et al. |
| 2015/0073406 A1 | 3/2015 | Molsberger |
| 2015/0165210 A1 | 6/2015 | Kilgore et al. |

(56) References Cited

U.S. PATENT DOCUMENTS

| | | | |
|---|---|---|---|
| 2015/0174397 A1* | 6/2015 | Bhadra | A61N 1/36064 607/117 |
| 2015/0182742 A1 | 7/2015 | Ackermann et al. | |
| 2015/0238764 A1 | 8/2015 | Franke | |
| 2016/0101286 A1 | 4/2016 | Bhadra et al. | |
| 2016/0158542 A1 | 6/2016 | Ahmed | |
| 2016/0235969 A1 | 8/2016 | Kilgore et al. | |
| 2016/0235990 A1 | 8/2016 | Mashiach | |
| 2016/0243353 A1 | 8/2016 | Ahmed | |
| 2016/0256689 A1 | 9/2016 | Vallejo et al. | |
| 2016/0263381 A1 | 9/2016 | Ahmed et al. | |
| 2016/0271392 A1 | 9/2016 | Vallejo et al. | |
| 2016/0271413 A1 | 9/2016 | Vallejo et al. | |
| 2016/0331326 A1 | 11/2016 | Xiang et al. | |
| 2016/0346533 A1 | 12/2016 | Bhadra et al. | |
| 2017/0028192 A1 | 2/2017 | Ahmed et al. | |
| 2017/0080244 A1 | 3/2017 | Chiel et al. | |
| 2017/0100591 A1 | 4/2017 | Nudo et al. | |
| 2017/0136235 A1 | 5/2017 | Molsberger | |
| 2017/0312505 A1 | 11/2017 | Ahmed | |
| 2018/0028824 A1 | 2/2018 | Pivonka et al. | |
| 2018/0256886 A1 | 9/2018 | Bhadra et al. | |
| 2018/0361155 A1 | 12/2018 | Bhadra et al. | |
| 2019/0060640 A1 | 2/2019 | Bhadra et al. | |
| 2019/0167996 A1 | 6/2019 | Bhadra et al. | |
| 2019/0184160 A1 | 6/2019 | Franke et al. | |
| 2019/0184173 A1 | 6/2019 | Franke | |
| 2019/0269921 A1 | 9/2019 | Bhadra et al. | |
| 2019/0314630 A1 | 10/2019 | Ackermann et al. | |
| 2020/0001073 A1 | 1/2020 | Bhadra et al. | |

FOREIGN PATENT DOCUMENTS

| | | |
|---|---|---|
| JP | 2009529352 | 8/2009 |
| JP | 2011502022 | 1/2011 |
| JP | 2011512991 | 4/2011 |
| WO | 2007/082382 | 7/2007 |
| WO | 2008/140376 | 11/2008 |
| WO | 2010/042750 | 4/2010 |
| WO | 2011/159527 A2 | 12/2011 |
| WO | 2013/052793 A1 | 4/2013 |
| WO | 2013/188753 | 12/2013 |
| WO | 2015/142838 | 9/2015 |
| WO | 2017/044542 | 3/2017 |
| WO | 2017/062272 | 4/2017 |
| WO | 2017/106519 A1 | 6/2017 |
| WO | 2018/085611 | 5/2018 |
| WO | 2018/187237 | 10/2018 |
| WO | 2019/157285 | 8/2019 |
| WO | 2019/164952 | 8/2019 |
| WO | 2020/010020 | 1/2020 |

OTHER PUBLICATIONS

Canadian Examination Report for corresponding Canadian Application Serial No. 2,876,297, dated Mar. 14, 2017, pp. 1-4.

PCT International Search Report and Written Opinion for PCT/US2013/045859, dated Oct. 9, 2013, pp. 1-5.

Canadian Office Action for corresponding Canadian Application Serial No. 3,008,024, dated Feb. 18, 2020, pp. 1-6.

Japanese Office Action for corresponding Japanese Application Serial No. 2018-199118, dated Jan. 7, 2020, pp. 1-4.

Ackermann, Jr, D. Michael, et al. "Separated interface nerve electrode prevents direct current induced nerve damage." Journal of neuroscience methods 201.1 (2011): 173-176.

Bhadra, Niloy, and Kevin L. Kilgore. "Direct current electrical conduction block of peripheral nerve." IEEE Transactions on Neural Systems and Rehabilitation Engineering 12.3 (2004): 313-324.

Borsook, David. "A future without chronic pain: neuroscience and clinical research." Cerebrum: the Dana forum on brain science. vol. 2012. Dana Foundation, 2012.

Brummer, S.B. et al. "Electrical Stimulation of the Nervous System: The Principle of Safe Charge Injection with Noble Metal Electrodes." Bioelectrochemistry and Bioenergetics 2: (1975) 13-25.

Bussel, Catelijne M., Dirk L. Stronks, and Frank JPM Huygen. "Successful treatment of intractable complex regional pain syndrome type I of the knee with dorsal root ganglion stimulation: a case report." Neuromodulation: Technology at the Neural Interface 18.1 (2015): 58-61.

Cogan, S.F., et al. "In Vitro Comparison of the Charge-Injection Limits of Activated Iridium Oxide (AIROF) and Platinum-Iridium Microelectrodes", IEEE Transactions on Biomedical Engineering, 52.9 (2005): 1612-1614.

Cogan, S.F., et al. "Potential-Biased, Asymmetric Waveforms for Charge-Injection With Activated Iridium Oxide (AIROF) Neural Stimulation Electrodes." 2006: 53(2): 327-332.

Donaldson et al. "When are actively balanced biphasic ('Lilly') stimulating pulses necessary in a neurological prosthesis?" Medical & Biological Engineering & Computing Jan. 1986: 24: 41-49.

Elbasiouny, S., et al. Modulation of motoneuronal firing behavior after spinal cord injury using intraspinal microstimulation current pulses: a modeling study. J. Appl. Physiol. 103 (2007) 276-286.

Fridman, Gene Y., and Charles C. Della Santina. "Safe direct current stimulation to expand capabilities of neural prostheses." IEEE Transactions on Neural Systems and Rehabilitation Engineering 21.2 (2013): 319-328.

Fridman, Gene Y., and Charles C. Della Santina. "Safe direct current stimulator 2: concept and design." In Engineering in Medicine and Biology Society (EMBC), 2013 35th Annual International Conference of the IEEE, pp. 3126-3129. IEEE, 2013.

Gabrielsson, Erik O., et al. "A four diode full wave ionic current rectifier based on bipolar membranes: Overcoming the limit of electrode capacity." Advanced Materials 26.30 (2014): 5143-5147.

Hasegawa, G., et al. "Impact of Electrolyte on Pseudocapacitance and Stability of Porous Titanium Nitride (TiN) Monolithic Electrode", Journal of the Electrochemical Society, 162.1 (2015): A77-A85.

Hollingworth, Milo, et al. "Single Electrode Deep Brain Stimulation with Dual Targeting at Dual Frequency for the Treatment of Chronic Pain: A Case Series and Review of the Literature." Brain sciences 7.1 (2017): 1-11.

Holtzheimer, Paul E., and Helen S. Mayberg. "Deep brain stimulation for psychiatric disorders." Annual review of neuroscience 34 (2011): 289-307.

Huang, C. et al. "Electrical stimulation of the auditory nerve: direct current measurement in vivo." IEEE Transactions on Biomed. Eng. vol. 46 No. 4 Apr. 1999 at 461-470.

Hurlbert, R. John. "Dose-response study of the pathologic effects of chronically applied direct current stimulation on the normal rat spinal cord." J. Neurosurg. 79 (Dec. 1993) 905-916.

Keifer, Orion Paul, Jonathan P. Riley, and Nicholas M. Boulis. "Deep brain stimulation for chronic pain: intracranial targets, clinical outcomes, and trial design considerations." Neurosurgery Clinics 25.4 (2014): 671-692.

Kim et al. "Electrochemical studies on the alternating current corrosion of mild steel under cathodic protection condition in marine environments", Electrochimica Acta 51, 2006, p. 5259-5267.

Krum, Henry, et al. "Catheter-based renal sympathetic denervation for resistant hypertension: a multicentre safety and proof-of-principle cohort study." The Lancet 373.9671 (2009): 1275-1281.

Kumsa, D et al. Electrical neurostimulation with imbalanced waveform mitigates dissolution of platinum Electrodes. J. Neural Eng. 13 (2016): 1-5.

Kumsa, D et al. Electrical neurostimulation with imbalanced waveform mitigates dissolution of platinum electrodes. Neural Eng. (2018) 13(5): 1-8.

Kumsa, D.W., et al. "Electron transfer processes occurring on platinum neural stimulating electrodes: pulsing experiments for cathodic-first, charge-imbalanced, biphasic pulses for 0.566 ? k ? 2.3 in rat subcutaneous tissues", Journal of Neural Engineering, 16 (2019): 1-11.

McHardy, J., et al., "An Approach to Corrosion Control during Electrical Stimulation", Annals of Biomedical Engineering, 5 (1977): 144-149.

(56) References Cited

OTHER PUBLICATIONS

Mendell, Lorne M. "Constructing and deconstructing the gate theory of pain." PAIN® 155.2 (2014): 210-216.
Merrill, Daniel R., Marom Bikson, and John GR Jefferys. "Electrical stimulation of excitable tissue: design of efficacious and safe protocols." Journal of neuroscience methods 141.2 (2005): 171-198.
Mortimer, J.T., et al., "Intramuscular Electrical Stimulation: Tissue Damage", Annals of Biomedical Engineering, 8 (1980): 235-244.
Nahin, Richard L. "Estimates of pain prevalence and severity in adults: United States, 2012." The Journal of Pain 16.8 (2015): 769-780.
Nakajima, H., et al. "Cervical angina: a seemingly still neglected symptom of cervical spine disorder?" Spinal cord 44.8 (2006): 509-513.
Neupane, M et al. Study of Anodic Oxide Films of Titanium Fabricated by Voltammetric Technique in Phosphate Buffer Media. Int. J. Electrochem. Sci., 4 (2009) 197-207.
Nielsen et al., "AC-Corrosion and Electrical Equivalent Diagrams", in: Proceedings of 5th International Congress, CeoCo, bruxelles, Belgium, 2000.
Schaldach M, Fractal Coated Leads: Advanced Surface Technology of Genuiune Sensing and Pacing, Progress in Biomedical Research, (2000): 259-272.
Scheiner, A., et al., "Imbalanced Biphasic Electrical Stimulation: Muscle Tissue Damage", Annals of Biomedical Engineering, 18 (1990): 407-425.
Specht, H. et al., Electrochemical properties and stability of PVD coatings for the application in cardiac and neurological stimulation, (2006).
TJEPKEMACloostermans, Marleen C., et al. "Effect of burst stimulation evaluated in patients familiar with spinal cord stimulation." Neuromodulation: Technology at the Neural Interface 19.5 (2016): 492-497.
Yang, Fei, et al. "Differential expression of voltage-gated sodium channels in afferent neurons renders selective neural block by ionic direct current." Science advances 4.4 (2018): eaaq1438 in 10 pages.

* cited by examiner

SYSTEMS FOR TREATMENT OF A NEUROLOGICAL DISORDER USING ELECTRICAL NERVE CONDUCTION BLOCK

GOVERNMENT FUNDING

This work was supported, at least in part, by grant number R01-NS-074149 and grant number R01-EB-002091 from the Department of Health and Human Services, National Institutes of Health, National Institute of Neurological Disorders and Stroke. The United States government may have certain rights in this invention.

RELATED APPLICATIONS

This application is a U.S. National Stage under 35 USC 371 patent application claiming priority to Serial No. PCT/US2016/066960, filed on Dec. 15, 2016, which claims the benefit of U.S. patent application Ser. No. 14/969,826, filed Dec. 15, 2015 (Now U.S. Pat. No. 9,694,181), each of which is hereby incorporated by reference for all purposes.

TECHNICAL FIELD

The present disclosure generally relates to electrical nerve conduction block (ENCB), and more particularly to methods of treating a neurological disorder using ENCB without producing damaging electrochemical reaction products.

BACKGROUND

Many neurological disorders are characterized by abnormal conduction in one or more nerves, leading to unwanted neural activity. In some instances, the abnormal conduction can be associated with pain, spasticity, or other pathological effects realized by different end organs. Examples of neurological disorders can include stroke, brain injury, spinal cord injury (SCI), cerebral palsy (CP), and multiple sclerosis (MS), as well as cancer, joint replacement, endometriosis, hyperhidrosis, vertigo, sialorrhea, torticollis, neuroma, hiccups, and the like. Traditionally, these neurological disorders have been treated using drugs or invasive methods, like neurolysis. Although generally not clinically used, these neurological disorders also can be treated by blocking conduction in the peripheral axons to stop the unwanted neural activity through application of a high frequency alternating current (HFAC) waveform and/or a direct current (DC) waveform.

HFAC waveforms have been shown to provide a localized, immediate, complete, and reversible conduction block without causing electrochemical damage. However, HFAC produces a transient onset response in the nerve, which can take many seconds to diminish and cease. The onset response has not yet been eliminated through modification of the HFAC waveform or electrode design alone. While it is possible to completely neutralize the onset response by applying a brief DC waveform through a flanking electrode, nerve conduction is lost after several applications of the DC waveform. The loss of conduction may be due to the creation of damaging electrochemical reaction products caused by the DC waveform at the levels of charge required to be injected to block conduction in the nerve.

Additionally, DC waveforms can be used as an alternative to HFAC block. Indeed, the DC waveforms can be designed to eliminate the unfavorable onset response or anodic break excitation. However, these DC waveforms can cause electrochemical damage to the nerve. For example, the damage can be due to the formation of damaging electrochemical reaction products, like free radicals, that can be created when the charge injection capacity of the interface is exhausted. The charge injection capacity (or "charge capacity") generally refers to an amount of charge that can be delivered by the electrode before voltage across the electrode-electrolyte interface leaves the water-window (a voltage in a cyclic voltammogram (CV) between the specific the production of molecular oxygen and molecular hydrogen).

SUMMARY

The present disclosure generally relates to electrical nerve conduction block (ENCB), and more particularly to methods of treating a neurological disorder using ENCB without producing damaging electrochemical reaction products. For example, the ENCB can be delivered to a nerve using a therapy delivery device (e.g., an electrode) that includes an electrode contact that includes (e.g., is made from, coated by, or the like) a high-charge capacity material capable of delivering a charge required to achieve the desired block of the nerve without the occurrence of irreversible electrochemical reactions. As an example, the high charge capacity material can include platinum black, iridium oxide, titanium nitride, tantalum, poly(ethylenedioxythiophene), of the like.

An aspect of the present disclosure includes a method for reducing pain in a subject. The method includes placing an electrode contact in electrical communication with a nerve that transmits a signal related to the pain. The method also includes applying an ENCB to the nerve through the electrode contact without causing electrochemical damage to the nerve. The electrode contact can include a high charge capacity material that prevents formation of damaging electrochemical reaction products at a charge delivered by the ENCB. The method also includes blocking transmission of the signal related to the pain through the nerve with the ENCB to reduce the pain.

Another aspect of the present disclosure includes a method for reducing muscle spasticity in a subject. The method includes placing an electrode contact in electrical communication with a nerve that transmits a signal related to the muscle spasticity. The method also includes applying an ENCB to the nerve through the electrode contact without causing electrochemical damage to the nerve. The electrode contact can include a high charge capacity material that prevents formation of damaging electrochemical reaction products at a charge delivered by the ENCB. The method also includes blocking transmission of the signal through the nerve with the ENCB to stop the muscle spasticity.

A further aspect of the present disclosure includes a method for treating a neurological disorder (e.g., hyperhidrosis, vertigo, sialorrhea, or the like) in a subject. The method includes placing an electrode in electrical communication with a nerve that transmits a signal related to the disorder. The method also includes applying an ENCB to the nerve through the electrode contact without causing electrochemical damage to the nerve. The electrode contact can include a high charge capacity material that prevents formation of damaging electrochemical reaction products at a charge delivered by the ENCB. The method further includes blocking transmission of the signal through the nerve with the ENCB to treat the disorder.

A further aspect of the present disclosure includes a system comprising a waveform generator, a controller, and an electrical contact. The waveform generator is for generating an electrical nerve conduction block (ENCB). The controller is coupled with the waveform generator. The controller is configured to receive an input comprising at least one parameter to adjust the ENCB. The electrical contact is coupled with the waveform generator. The electrical contact is configured to be placed into contact with a nerve. The electrical contact comprises a high charge capacity material that prevents formation of damaging electrochemical products at a charge delivered by the ENCB. The electrical contact is configured to deliver the ENCB to the nerve to block transmission of a signal related to a pain through the nerve.

BRIEF DESCRIPTION OF THE DRAWINGS

The foregoing and other features of the present disclosure will become apparent to those of skill in the art to which the present disclosure relates upon reading the following description with reference to the accompanying drawings in which.

DETAILED DESCRIPTION

I. Definitions

Figure 1:
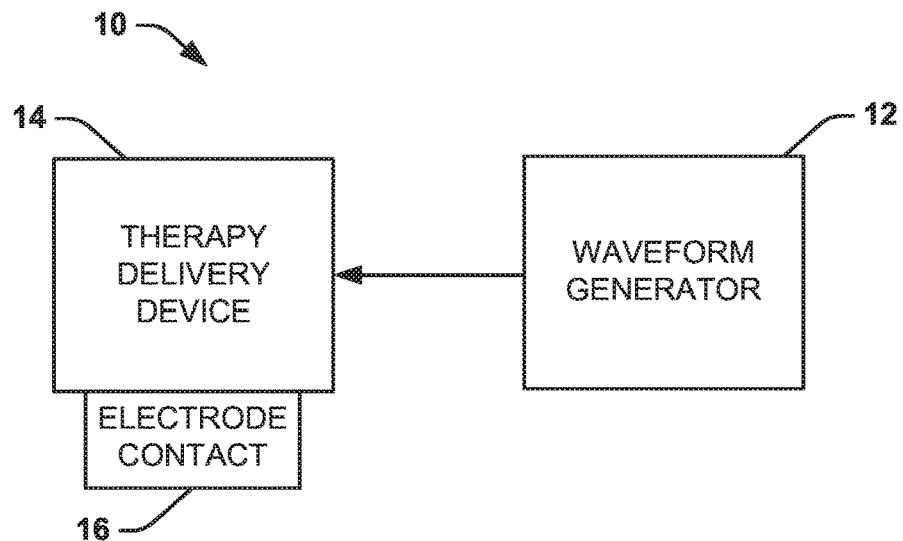
FIG. 1 is an illustration of an example system that can deliver electrical nerve conduction block (ENCB) to a nerve without causing electrochemical damage.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the terms "nerve block", "nerve conduction block", and "block" can be used interchangeably when referring to the failure of impulse transmission at some point along a nerve. In some instances, nerve conduction can be blocked by extinguishing an action potential at some point as it travels along the nerve. In other instances, nerve conduction can be blocked by increasing the activation threshold of a target nerve and/or decreasing the conduction velocity of a nerve, which can lead to an incomplete or substantial block of nerve conduction.

As used herein, nerve conduction is "blocked" when transmission of action potentials through a nerve is extinguished completely (e.g., 100% extinguished).

As used herein, nerve conduction is "substantially blocked" when an "incomplete nerve block" or "substantial nerve block" occurs. The terms "incomplete block" and "substantial block" can refer to a partial block, where less than 100% (e.g., less than about 90%, less than about 80%, less than about 70%, less than about 60%, or less than about 50%) of the action potentials traveling through a nerve are extinguished.

As used herein, the term "electrical nerve conduction block" or "ENCB" can refer to an external electrical signal (or waveform) that can generate an electric field sufficient to block the conduction in a nerve. The ENCB can include a direct current (DC) waveform (balanced charge biphasic, substantially balanced-charge biphasic, or monophasic) and/or a high frequency alternating current (HFAC) waveform.

As used herein, the term "DC waveform" can refer to a waveform that can include a current pulse of either polarity (e.g., either cathodic or anodic). In some instances, the DC can be applied as the first phase of a biphasic waveform. The second phase of the biphasic waveform can either reverse 100% of the total charge delivered by the first phase (as a charge-balanced biphasic waveform) or reverse less than 100% of the total charge delivered by the first phase, thereby reducing the production of damaging reaction products that can cause damage to the nerve and/or the electrodes used to deliver the DC. In other instances, the DC can be applied as a monophasic waveform.

As used herein, the term "high frequency" with reference to alternating current (e.g. HFAC) can refer to frequencies above approximately one kiloHertz (kHz), such as about 5 kHz to about 50 kHz.

As used herein, the term "electrical communication" can refer to the ability of an electric field to be transferred to a nerve and have a neuromodulatory effect (e.g. blocking neural signal transmission) within the nerve of a patient.

As used herein, an "electrical signal" (e.g., either voltage controlled or current controlled) can be applied to the axon, cell body or dendrites of a nerve (or population of nerves) so long as signal transmission (or conduction of action potentials) is blocked and the neural tissue is not damaged.

As used herein, the term "signal transmission" when associated with a nerve can refer to the conduction of action potentials within the nerve.

As used herein, the term "therapy delivery device" can refer to a device configured to deliver an ENCB to a nerve. In some examples, the therapy delivery device can include an electrode with one or more contacts. The one or more contacts can be made of a high charge capacity material that provides the conversion of current flow via electrons in a metal (wire/lead) to ionic means (in an electrolyte, such as interstitial fluid). In some instances, the electrode can aid in shaping the electric field generated by the contact(s). As an example, the electrode can be implantable and/or positioned on a skin surface of a patient.

As used herein, the term "high charge capacity material" can refer to a material that allows an electrode contact to deliver a charge necessary to block conduction in at least a portion of a nerve without damaging the nerve.

As used herein, the term "Q-value" can refer to a value of the total amount of charge that can be delivered through an electrode contact before causing irreversible electrochemical reactions, which can cause the formation of damaging reaction products. For example, the high charge capacity material can have a large Q-value, which enables a large charge to be delivered through the electrode contact before causing irreversible electrochemical reactions.

As used herein, the term "damaging reaction products" can refer to reactions that can damage the nerve, another part of the body in proximity to the electrode contact, and/or the electrode contact. For example, a damaging reaction product can be due to oxygen evolution or hydrogen evolution. As another example, a damaging reaction product can be due to dissolution of the material of an electrode contact. As used herein, an ENCB can be considered "safe" when the block occurs without producing damaging reaction products.

As used herein, the term "electrode/electrolyte interface" can refer to a double layer interface where a potential difference is established between the electrode and the electrolyte (e.g., an area of the patient's body, such as interstitial fluid).

As used herein, the term "geometric surface area" of an electrode contact can refer to a two-dimensional surface area of the electrode contact, such as a smooth surface on one side of the electrode contact as calculated by the length times the width of the two-dimensional outer surface of the electrode contact.

As used herein, the terms "effective surface area" and "true surface area" of an electrode contact can refer to the surface area that can be inferred from the area within the curve of a cyclic voltammogram ("CV") of the electrode contact.

As used herein, the term "waveform generator" can refer to a device that can generate an electric waveform (e.g., charge balanced biphasic DC, substantially charge balanced biphasic DC, monophasic DC, HFAC, or the like) that can be provided to an electrode contact to provide an ENCB. The waveform generator can be, for example, implantable within a patient's body and/or external to the patient's body.

As used herein, the term "nervous system" refers to a network of nerve cells and neural tissue that transmit electrical impulses (also referred to as action potentials) between parts of a patient's body. The nervous system can include the peripheral nervous system and the central nervous system. The peripheral nervous system includes motor nerves, sensory nerves, and autonomic nerves, as well as interneurons. The central nervous system includes the brain and the spinal cord. The terms "nerve" and "neural tissue" can be used interchangeably herein to refer to tissue of the peripheral nervous system or the central nervous system unless specifically described as referring to one, while excluding the other.

As used herein, the terms "disorder" and "neurological disorder" can be used interchangeably to refer to a condition or disease characterized at least in part by abnormal conduction in one or more nerves. In some instances, the abnormal conduction can be associated with pain and/or spasticity. Examples of neurological disorders can include stroke, brain injury, spinal cord injury (SCI), cerebral palsy (CP), and multiple sclerosis (MS), as well as cancer, joint replacement, endometriosis, hyperhidrosis, vertigo, sialorrhea, torticollis, neuroma, hiccups, and the like.

As used herein, the terms "patient" and "subject" can be used interchangeably and refer to any warm-blooded organism suffering from a neurological disorder. Example warm-blooded organisms can include, but are not limited to, a human being, a pig, a rat, a mouse, a dog, a cat, a goat, a sheep, a horse, a monkey, an ape, a rabbit, a cow, etc.

II. Overview

The present disclosure generally relates to electrical nerve conduction block (ENCB). The ENCB can block signal transmission (also referred to as "conduction" of action potentials) in one or more nerves to stop unwanted neural activity of a neurological disorder, such as pain, muscle spasticity, hyperhidrosis, vertigo, sialorrhea, and the like. However, traditionally, ENCB has not been utilized to treat unwanted neural activity in such neurological disorders. One reason for the reluctance to use ENCB is an occurrence of undesirable side effects, such as the generation of dangerous electrochemical reaction products. The high charge capacity electrode contacts of the present disclosure can substantially eliminate this electrochemical damage at charges used for the ENCB. Accordingly, the present disclosure relates to methods of treatment of a neurological disorder using ENCB without causing electrochemical damage to the nerve, the patient's body, or the electrode.

The ENCB can be delivered to a nerve using a therapy delivery device (e.g., an electrode) that includes an electrode contact comprising a high-charge capacity material. Using the high charge capacity material, the electrode contacts of the present disclosure can deliver the ENCB without the onset response characteristic of HFAC waveforms and also without the electrochemical damage due to application of DC waveforms. Generally, the high-charge capacity electrode can have a Q value above about 100 µC. In other words, the high-charge capacity electrode can deliver a charge above about 100 µC without the generation of irreversible reaction products. However, in some instances, the high-charge capacity electrode can have a Q value between about 1 µC and about 100 µC. In other instances, the high-charge capacity electrode can have a Q value on the order of about 10 µC.

Using the high-charge capacity material, more charge can be delivered safely for longer periods of time compared to traditional stimulation electrodes, such as those fabricated from platinum or stainless steel. In certain instances, the high-charge capacity material can have a charge injection capacity (the charge density that safely can be delivered through the material) of about 1 to about 5 mC/cm². In comparison, polished platinum, a non-high charge capacity material, has a charge injection capacity of about 0.05 mC/cm². With an electrode contact comprising a high charge capacity material, the effective surface area of the electrode contact is increased by several orders of magnitude over the geometric surface area. As such, as an example, DC can be safely delivered through monopolar nerve cuff electrode contacts for durations as long as ten seconds without any nerve damage. Accordingly, the present disclosure provides a superior block that is effective, reversible, and "no onset".

III. Systems

In some aspects, the present disclosure relates to a system 10 (FIG. 1) that can be used to treat a neurological disorder by blocking signal transmission through at least a portion of a target nerve associated with the disorder. The system 10 can apply an electrical nerve conduction block (ENCB) to the nerve to block the signal transmission in the nerve. Advantageously, the ENCB can be delivered at the required charge levels without causing the generation of electrochemical reaction products that cause electrochemical damage. For example, the ENCB can be used for motor nerve block, sensory nerve block, autonomic nerve block, block in the central nervous system, block of interneurons, or the like. As opposed to other types of block, like neurolysis, when the ENCB is no longer applied, normal conduction is restored to the nerve.

The system 10 can include a waveform generator 12 coupled to (e.g., through a wired connection or a wireless connection), and in electrical communication with, a therapy delivery device 14 that includes one or more electrode contacts 16. The waveform generator 12 can generate an electrical waveform (also referred to as an "ENCB waveform" or simply "ENCB") that can be used to block signal transmission through the nerve. In some instances, the electrical waveform can be a monophasic direct current (DC) waveform, a balanced charge biphasic DC waveform, and/or a substantially balanced charged biphasic DC waveform. In other instances, the waveform can be a high frequency alternating current (HFAC) waveform.

The therapy delivery device 14 can receive the generated electrical waveform and deliver the ENCB to a nerve (also referred to as "target nerve" or "neural tissue") through one or more electrode contacts 16 (monopolar and/or bipolar). For example, the waveform generator 12 can generate different waveforms to be applied at different times and/or through different electrode contacts. As an example, the waveform generator 12 can generate both a DC waveform and an HFAC waveform to be applied at different times. As another example, the waveform generator 12 can generate a plurality of DC waveforms with different timing characteristics to be applied by different electrode contacts 16.

The therapy delivery device 14 is able to deliver the ENCB without the formation of irreversible, damaging electrochemical reaction products at least because the one or more electrode contacts 16 can include a high charge capacity material. Generally, the high charge capacity material can be any material that can allow the electrode contact 16 to deliver an electric charge required for the desired nerve conduction block without forming irreversible and damaging reaction products. For example, the water window of the high charge capacity material can be widened so that the charge required for the block can be delivered without achieving hydrogen or oxygen evolution. Non-limiting examples of high charge capacity materials include platinum black, iridium oxide, titanium nitride, tantalum, poly(ethylenedioxythiophene), and suitable combinations.

In some examples, the one or more electrode contacts 16 can be fabricated from the high charge capacity material. In other examples, the one or more electrode contacts 16 can include an electrically conductive material (e.g., platinum, stainless steel, or the like) that is coated, at least in part, by the high charge capacity material. In still other examples, the one or more electrode contacts 16 can include both electrode contacts fabricated from the high charge capacity material and electrode contacts coated, at least in part, by the high charge capacity material. In further examples, the one or more electrode contacts 16 can include both contacts that include the high charge capacity material and other contacts that do not include the high charge capacity material.

In one example, the one or more electrode contacts 16 can have a geometric surface area of at least about 1 mm². In another example, the geometric surface area of one or more electrode contacts 16 can be between about 3 mm² to about 9 mm². In some examples, each of the one or more electrode contacts 16 can have about equal geometric surface areas. In other examples, the one or more electrode contacts 16 can have different geometric surface areas.

Figure 2:
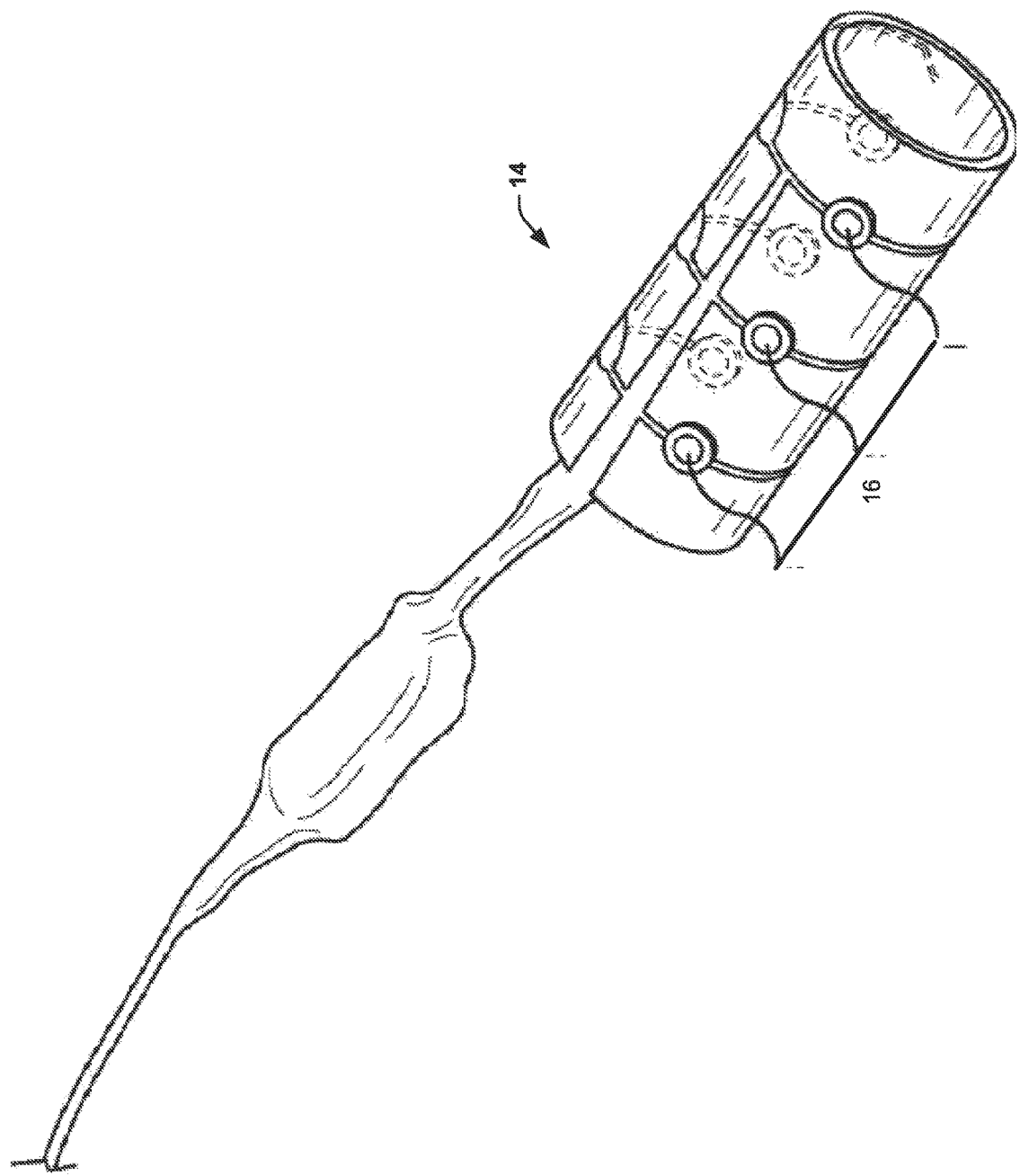
FIGS. 2 and 3 are examples of different therapy delivery devices that can be used by the system shown in FIG. 1.
Figure 3:
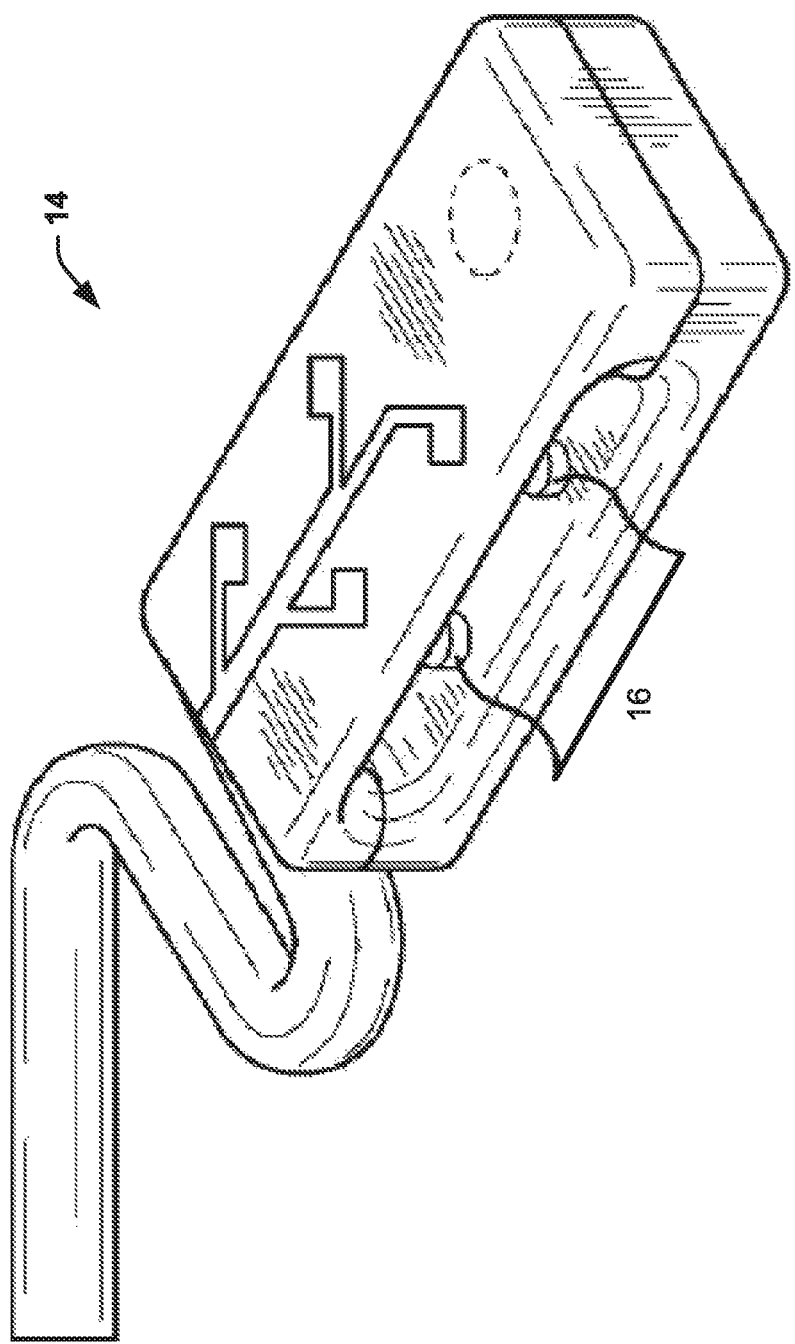

In some instances, the therapy delivery device 14 can be an electrode. In certain non-limiting examples, the therapy delivery device 14 can be an electrode (e.g., a nerve cuff electrode shown in FIG. 2 or a flat interface nerve electrode (FINE) shown in FIG. 3) that includes a plurality of multiple contiguous electrode contacts 16. However, the therapy delivery device 14 can have other configurations, which are not shown, such as a helical cuff or other nerve cuff electrode, a mesh, a linear rod-shaped lead, paddle-style lead, a disc contact electrode including a multi-disc contact electrode, or a penetrating intraneural electrode.

Figure 4:
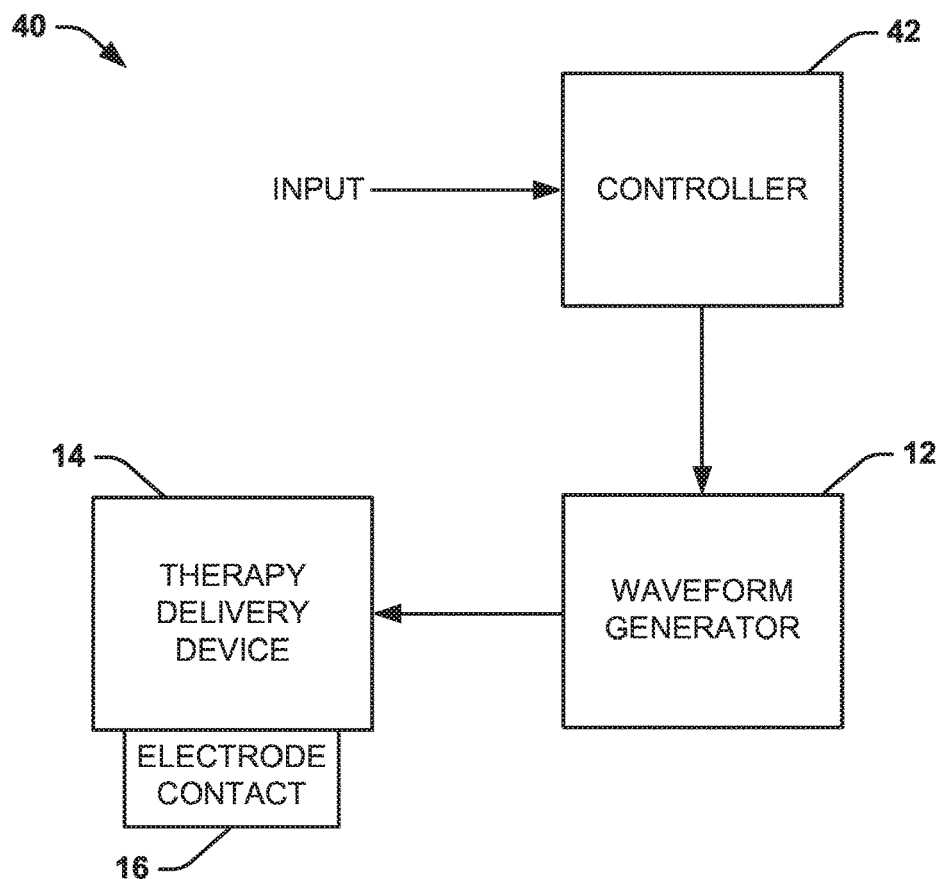
FIG. 4 is an illustration of an example system that can control the waveform generator in FIG. 1 according to an input.

Shown in FIG. 4 is an example system 40 that can control the parameters of the electrical waveform generated by the waveform generator 12. The system 40 can include a controller 42 that can receive an input (including at least one parameter) and signal the waveform generator 12 to adjust and/or deliver the electrical waveform to the therapy delivery device 14 so that an appropriate ENCB can be delivered to the nerve. For example, based on the input, the controller 42 can specify a timing parameter, an intensity parameter, a waveform parameter, and/or designate which of the one or more electrode contacts 16 is to deliver the ENCB. In one example, the controller 42 can specify an intensity parameter so that a portion of the signal transmission through the nerve is stopped (also referred to as "adjusting a degree of the block"). By blocking only a portion of the signal transmission, a negative result of the signal transmission can be reduced or eliminated, while still allowing the signal transmission through the rest of the nerve (such as allowing voluntary movement of a muscle, while blocking spasticity of the muscle).

In some instances, the controller 42 can be part of an open loop control system, in which the input is a user input from a patient (which can be bounded by a range of "safe" parameters predefined by a medical professional) or a medical professional. For example, the input can be made via an analog device (like a switch, dial, or the like), allowing the user to input an analog value. As another example, the input can be made via a digital device (like a keyboard, microphone, or the like), which can allow the user to input a digital value. The controller 42 can interpret the input and signal the waveform generator 12 including a parameter adjusted based on the input.

In other instances, the controller 42 can be part of a closed loop control system that can receive the input from an entity other than a user. For example, the closed loop control system can employ one or more sensors that can sense a change in a physiological parameter. The input can be based on the sensed change. The controller 42 can interpret the input and signal the waveform generator 12 including a parameter adjusted based on the input.

IV. Methods

Another aspect of the present disclosure can include methods that can be used to treat a neurological disorder by blocking signal transmission through at least a portion of a nerve associated with the neurological disorder with electrical nerve conduction block (ENCB). The ENCB can be applied via a monophasic direct current (DC) waveform, a balanced charge biphasic DC waveform, and/or a substantially balanced charged biphasic DC waveform. As another example, the ENCB can include a high frequency alternating current (HFAC) waveform. Advantageously, the ENCB can be applied without causing negative side effects, such as electrochemical damage at levels of charge injection required for the ENCB.

Figure 5:
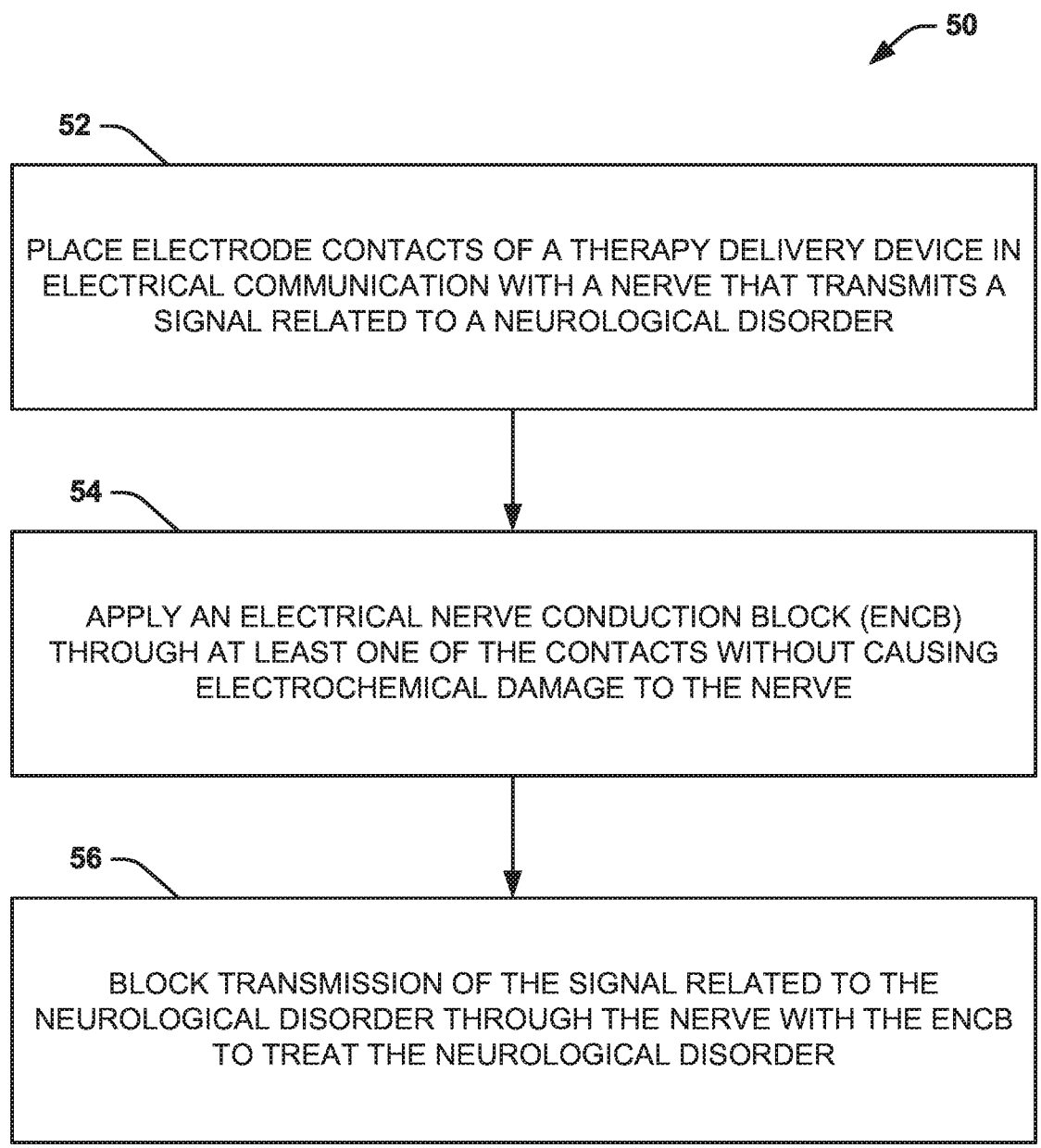
FIG. 5 is a process flow diagram illustrating an example method for delivering ENCB to a nerve without causing electrochemical damage.
Figure 6:
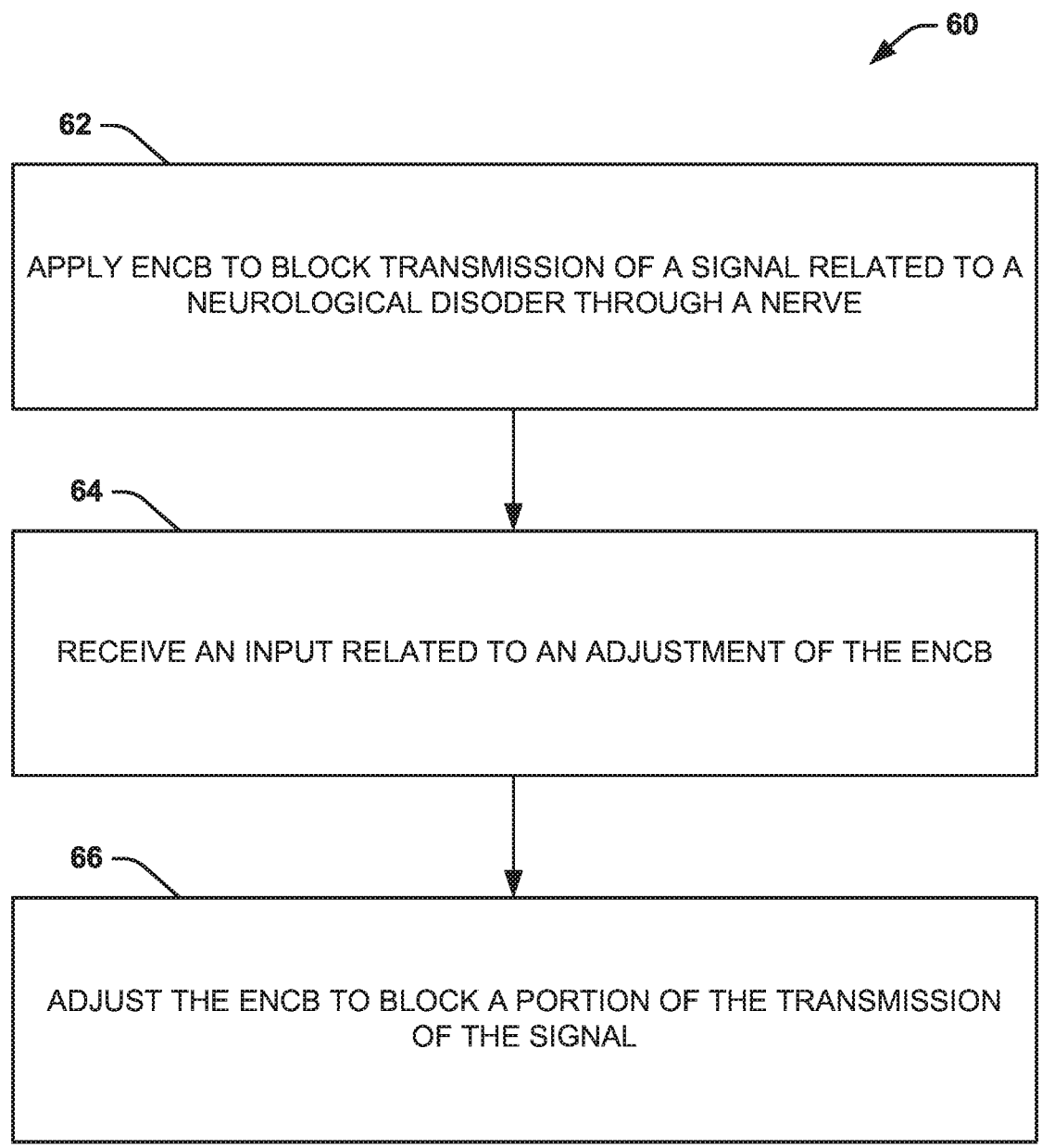
FIG. 6 is a process flow diagram illustrating an example method for adjusting a degree of ENCB applied to the nerve.

An example of a method 50 for delivering ENCB to a nerve without causing electrochemical damage is shown in FIG. 5. An example of a method 60 for adjusting a degree of ENCB applied to a nerve is shown in FIG. 6. The methods 50 and 60 can be applied, for example, using the systems as shown in FIGS. 1 and 4. The methods 50 and 60 of FIGS. 5 and 6, respectively, are illustrated as process flow diagrams with flowchart illustrations. For purposes of simplicity, the methods 50 and 60 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 50 and 60.

Referring now to FIG. 5, illustrated is an example of a method 50 for delivering ENCB to a nerve without causing electrochemical damage. At 52, electrode contacts of a therapy delivery device (e.g., the one or more electrode contacts 16 of the therapy delivery device 14) can be placed in electrical communication with a nerve that transmits a signal related to a neurological disorder. At least one of the electrode contacts can include (e.g., be constructed from, coated with, or the like) a high charge capacity material. The high charge capacity material allows the electrode contacts to deliver the charge required for conduction block without forming irreversible and damaging reaction products. For example, the high charge capacity material can allow the electrode to deliver at least 100 □C before irreversible electrochemical reactions take place in the material. However, in some instances, the high-charge capacity electrode can have a Q value between about 1 µC and about 100 µC. In other instances, the high-charge capacity electrode can have a Q value on the order of about 10 µC. Non-limiting examples of high charge capacity materials include platinum black, iridium oxide, titanium nitride, tantalum, poly(ethylenedioxythiophene), and suitable combinations.

At 54, an ENCB can be applied through at least one of the contacts without causing electrochemical damage to the nerve. In other words, the high charge capacity material enables the one or more contacts to deliver the charge required to block the conduction in the nerve without undergoing irreversible electrochemical reactions, and thereby damaging reaction products. At 56, transmission of a signal related to the neurological disorder (e.g., conduction of action potentials) can be blocked to treat the neurological disorder. The ENCB is reversible, so that when transmission of the ENCB is stopped, normal signal transmission through the nerve can be restored.

Referring now to FIG. 6, illustrated is an example of a method 60 for adjusting a degree of ENCB applied to a nerve. At 62, an ENCB (e.g., generated by a waveform generator 12 at a first level with first parameters) can be applied to a nerve (e.g., by therapy delivery device 14) to block transmission of a signal related to a neurological disorder (e.g., conduction of action potentials) through the nerve. At 64, an input (e.g., an input to controller 42) can be received. The input can be from a user (e.g., a patient, a medical professional, or the like) or can be automated (e.g., from one or more sensors that detect one or more physiological parameters). In other words, method 60 can be operated as open loop control and/or closed loop control. At 66, the ENCB can be adjusted (e.g., one or more parameters of the ENCB) can be adjusted to block a portion of the transmission of the signal. In other words, the ENCB can be adjusted so that only a portion of action potentials through the nerve (or population of nerves) are blocked from conducting, while another portion of action potentials is permitted to conduct through the nerve.

V. Examples—Electrode Construction and Waveform Design

The following examples illustrate construction of high charge capacity electrode contacts, as well as the design of various waveforms that can be delivered by the electrode contacts without causing nerve damage. The electrode contacts can deliver ENCB to any nerve (including peripheral nerves and/or central nervous system structures) by transmitting a desired electrical electric field trough the tissue to a desired neural structure. Specific waveforms are described as examples, but it will be understood that the waveform used for the ENCB in practice can include a direct current waveform (e.g., balanced charge biphasic, substantially balanced-charge biphasic, or monophasic) and/or a high frequency alternating current (HFAC) waveform.

High Charge Capacity Electrode Contacts

In this example, electrode contacts were fabricated from high charge capacity ("Hi-Q") materials to achieve ENCB without causing electrochemical damage to the nerve. The Hi-Q materials resulted in a significant increase of the electrode contact's charge injection capacity, quantified in the Q-value, which can be defined as the amount of charge that the electrode contact is capable of delivering before irreversible electrochemical reactions take place in or due to the material. One example of a Hi-Q material used in this experiment is platinized Pt (also referred to as platinum black). The platinized Pt is shown to be able to deliver DC nerve block to a nerve without causing electrochemical damage to the nerve, even after a large number (e.g., >100) of repeated applications.

Figure 7:
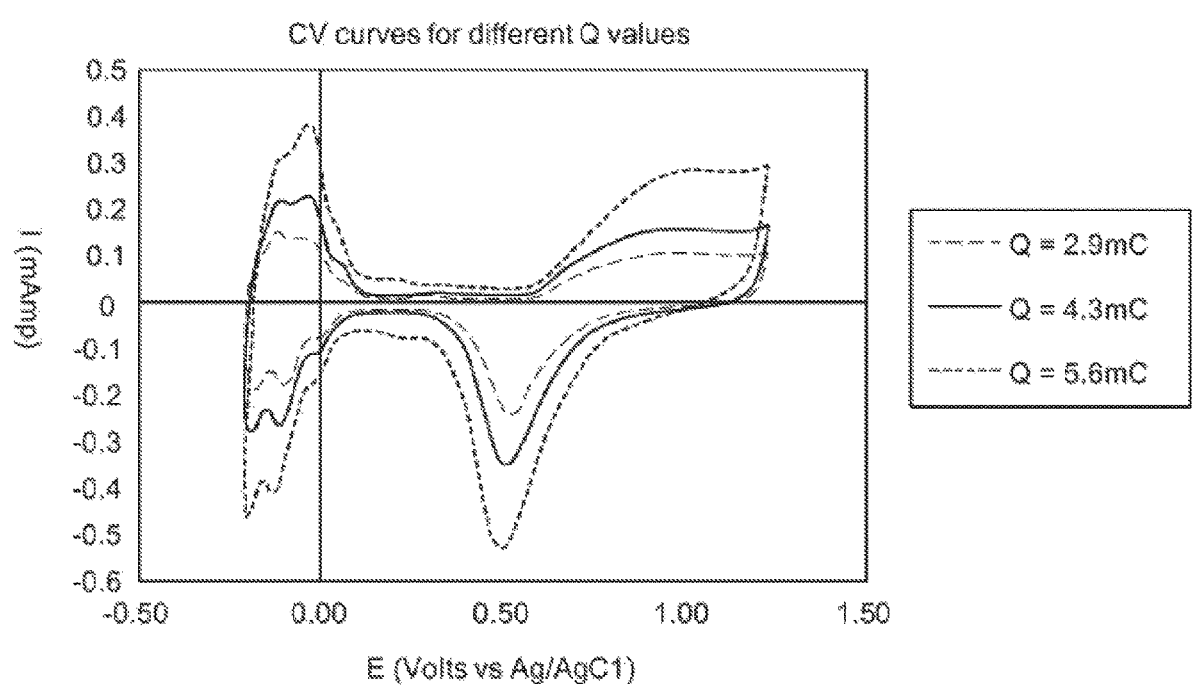
FIG. 7 is a cyclic voltammogram of several platinum black electrode contacts with different Q values.

Platinized Pt electrode contacts were constructed as follows. Monopolar nerve cuff electrode contacts were manufactured using platinum foil. These electrode contacts were then platinized in chloroplatinic acid solutions to create platinum black coatings of various roughness factors from 50 to over 600. A cyclic voltammogram for different platinum black electrode contacts was generated in 0.1M $H_2SO_4$ (shown in FIG. 7) to determine the water window, and thereby the amount of charge that can be safely delivered, for the platinized Pt.

The amount of charge that could be safely delivered by the platinized Pt electrode contacts (the Q value) was estimated by calculating the charge associated with hydrogen adsorption from −0.25V to +0.1V vs. a standard Ag/AgCl electrode contact. Typically Q values for these platinized Pt electrode contacts ranged from 2.9 mC to 5.6 mC. In contrast, a standard Pt foil electrode contact has a Q value of 0.035 mC.

Figure 8:
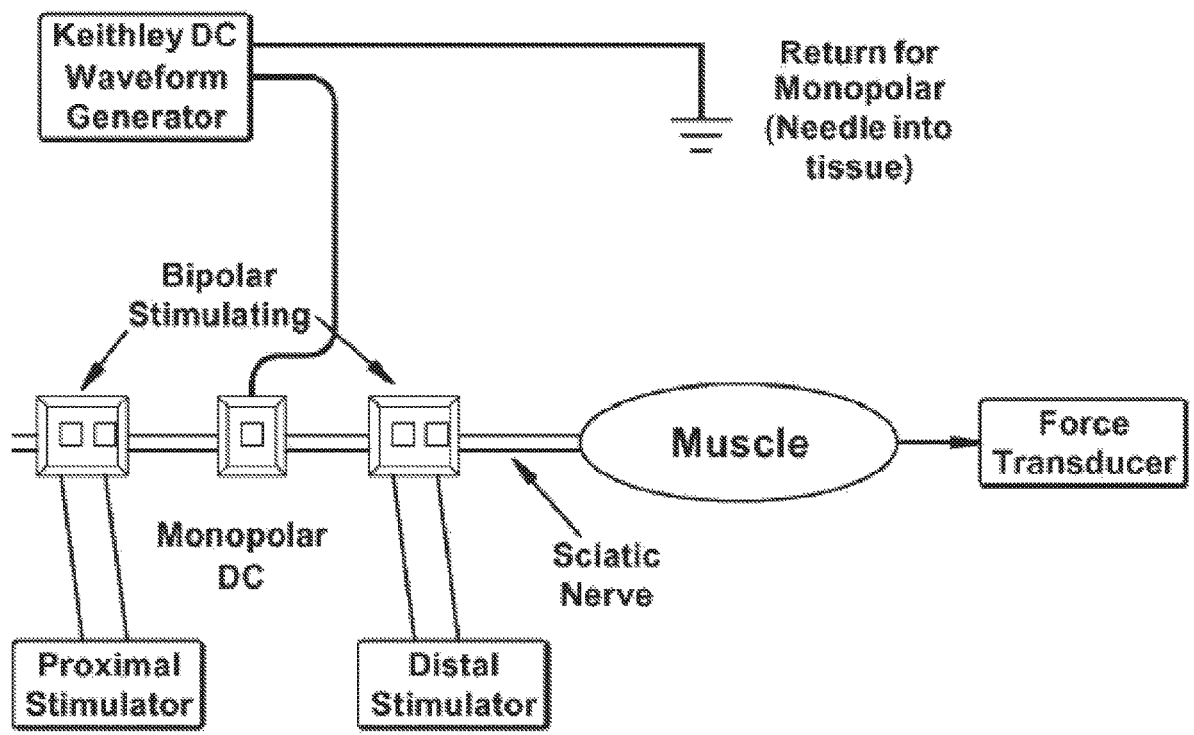
FIG. 8 is a diagram depicting one example of a system for using a DC ENCB to block nerve signal transmission without damaging the nerve.

Acute experiments were performed on Sprague-Dawley rats to test the efficacy of DC nerve block with both the platinized Pt electrode contacts and the control Pt electrode contacts. Under anesthesia, the sciatic nerve and the gastronomies muscle on one side was dissected. Bipolar stimulating electrode contacts were placed proximally and distally on the sciatic nerve. The proximal stimulation (PS) elicited muscle twitches and allowed the quantification of motor nerve block. The distal stimulation also elicited muscle twitches, which were compared with those from PS as a measure of nerve damage under the DC monopolar electrode contact. The monopolar electrode contact was placed between the two stimulating electrode contacts as schematically illustrated in FIG. 8.

A current-controlled waveform generator (Keithley Instruments, Solon, Ohio) was used to create the DC waveform. The waveform was biphasic, including a trapezoidal blocking phase followed by a square recharge phase as depicted in the lower graph (B) of FIG. 9. The ramp up and down ensured that there was no onset firing from the DC. The DC parameters were chosen so that the total charge delivered was less than the Q value for a given electrode contact. Each cathodic (blocking) pulse was then followed by a recharge phase in which 100% of the charge was returned to the electrode contact by an anodic pulse maintained at 100 µA.

Figure 9:
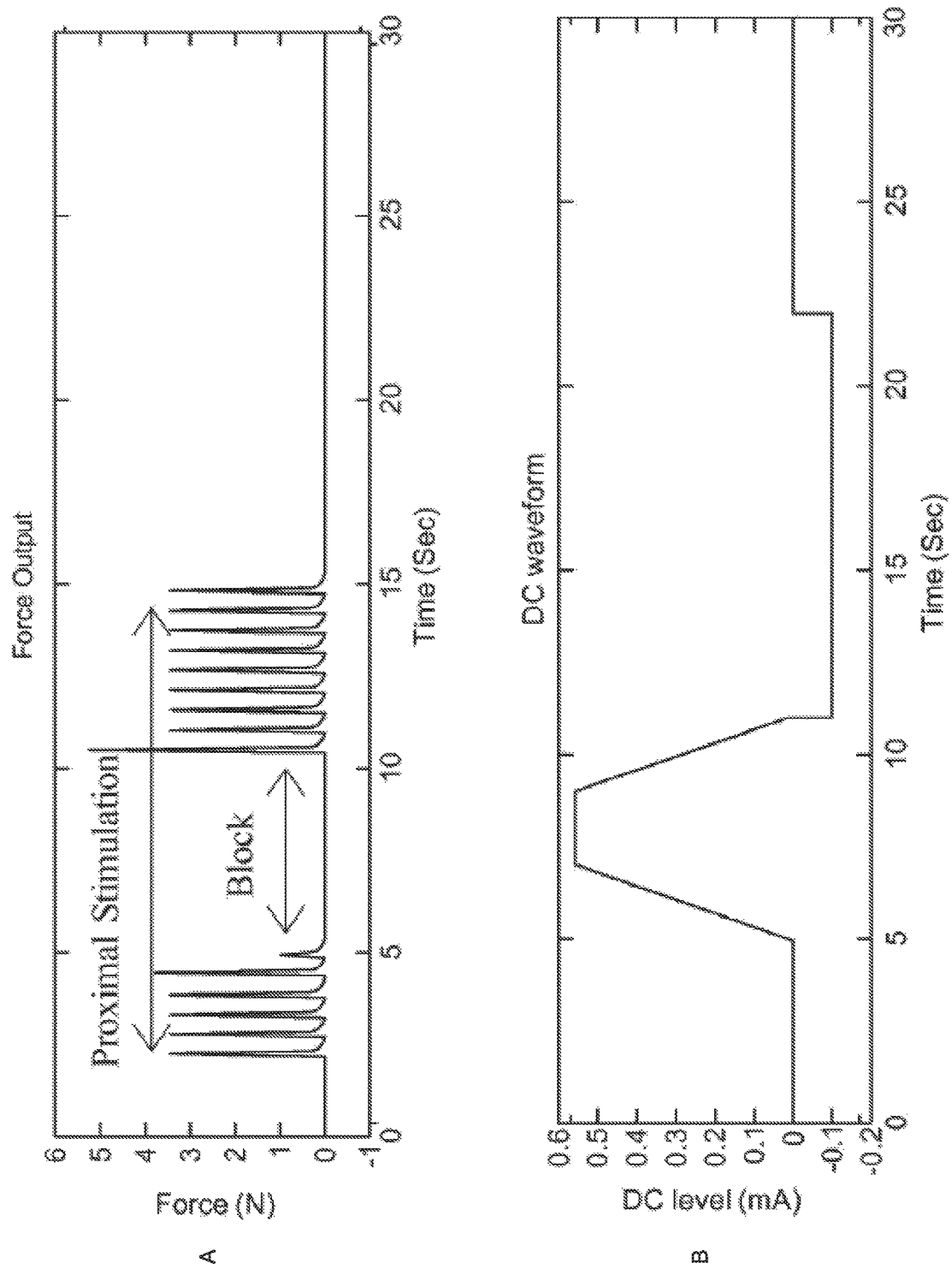
FIG. 9 is an illustrative DC block trial showing that the twitches elicited by proximal stimulation are blocked during the blocking phase of a trapezoidal waveform.

The platinized Pt electrode contacts achieved a conduction block, while maintaining the total charge below the maximum Q value for each electrode contact. FIG. 9 illustrates a trial where complete motor nerve block was obtained using the DC waveform with a peak amplitude of 0.55 mA. The muscle twitches elicited by PS were completely blocked during the plateau phase of the DC delivery, as shown in the upper graph (A) of FIG. 9.

Figure 10:
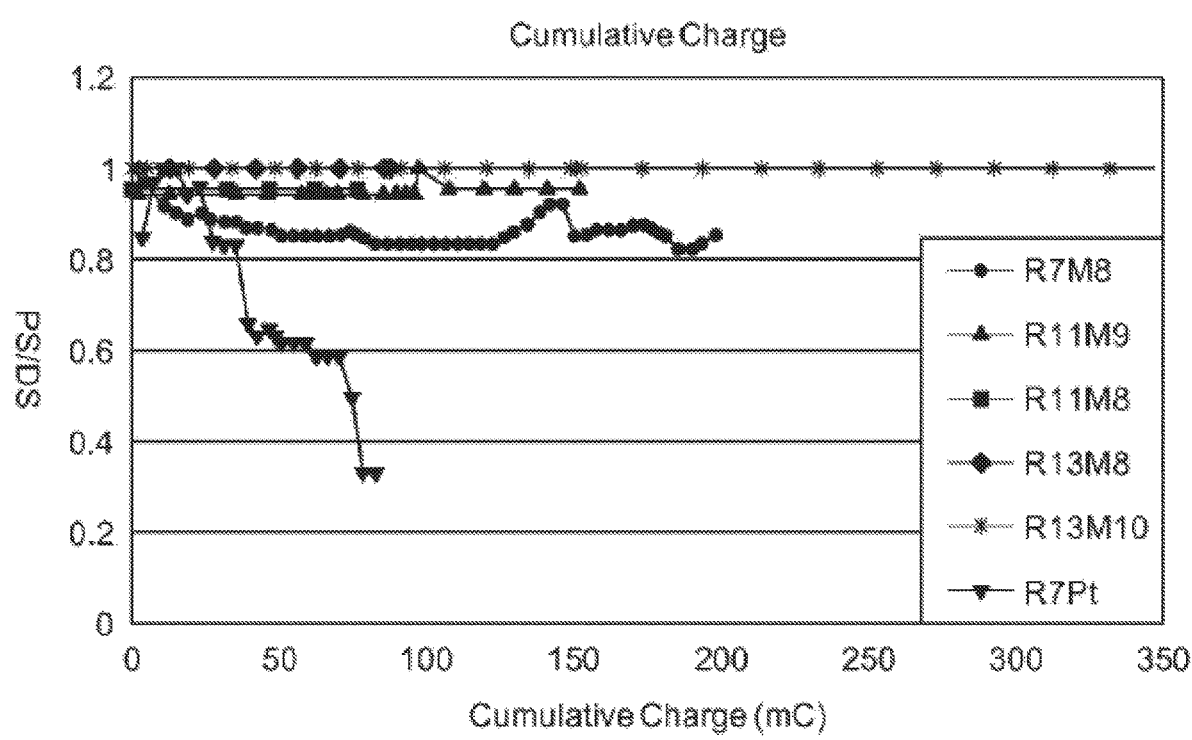
FIG. 10 is an illustration of the viability of sciatic nerve conduction following DC ENCB.

FIG. 10 illustrates the effects of cumulative dosages of DC for five of the platinized Pt electrode contacts as compared to a standard platinum electrode contact. DC was delivered as shown in FIG. 9 (lower subplot). Each cycle of DC was followed by PS and DS to produce a few twitches (not shown in FIG. 10). The PS/DS ratio is a measure of acute nerve damage. If the nerve is conducting normally through the region under the block electrode contact, the ratio should be near one. The platinum electrode contact demonstrated nerve damage in less than one minute after delivery of less than 50 mC and the nerve did not recover in the following 30 minutes. The platinized Pt electrode contacts do not show signs of significant neural damage for the duration of each experiment, up to a maximum of 350 mC of cumulative charge delivery. Similar results were obtained in repeated experiments using other platinized Pt electrode contacts with variable Q values.

Multi-Phase DC Waveform ENCB

Figure 11:
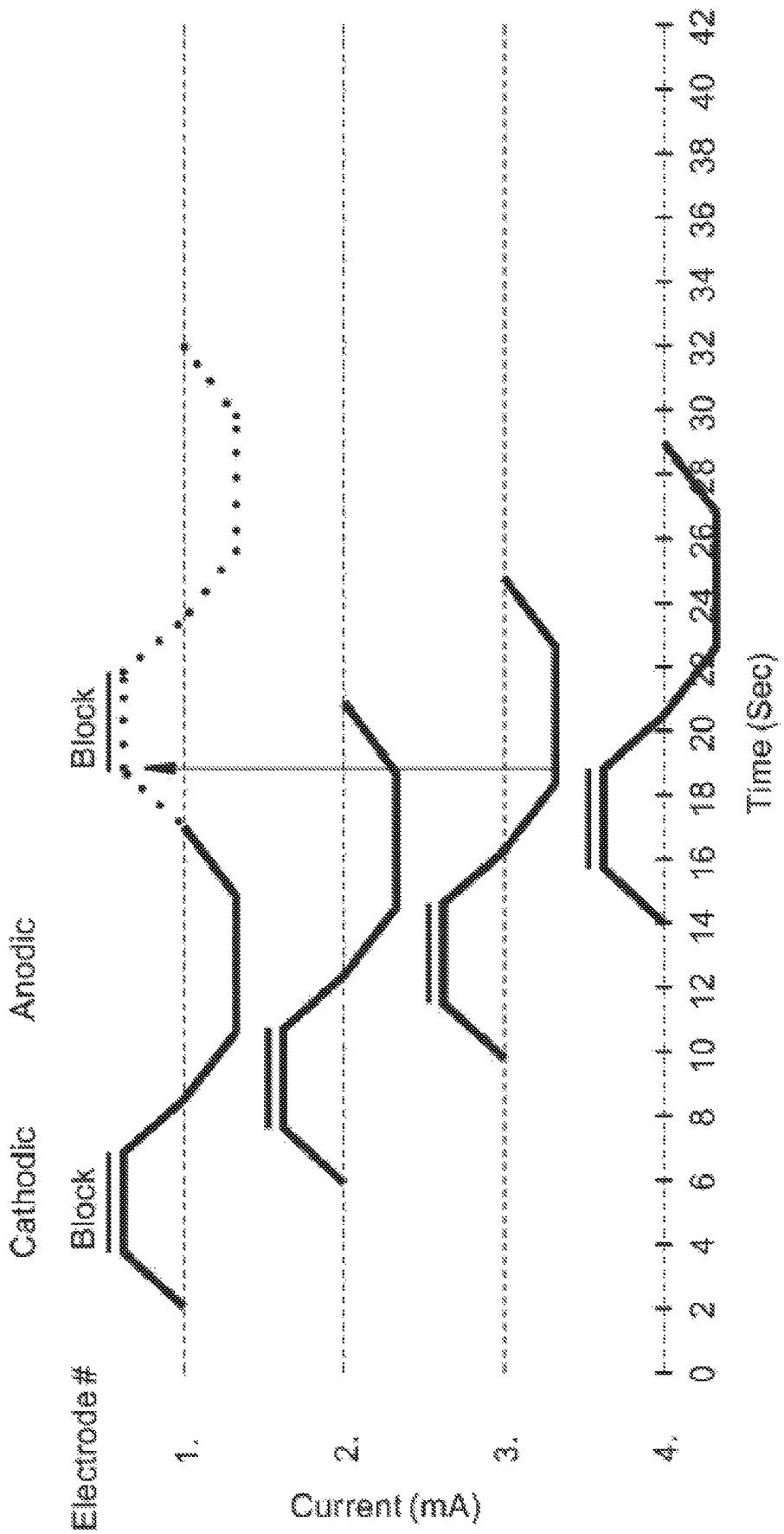
FIG. 11 is an illustration of an example of a multi-phase DC ENCB waveform.

In one example, the ENCB waveform includes a multi-phase DC. As shown in FIG. 11, the multi-phase DC can include a cathodic DC phase and a reciprocal anodic DC phase that are continuously cycled amongst four contiguous monopolar electrode contacts so that there will be a continuous neural block without neural damage. In some instances, the multi-phase DC can be charge balanced or substantially charge balanced so that stored charge was retrieved after the blocking time by inverting the current drive and charge-balancing the Helmholtz Double Layer (HDL).

It will be understood that the cathodic DC need not be applied first. As such, a multi-phase DC can be applied to the neural tissue including applying an anodic DC current and then a reciprocal cathodic DC current. One phase of the DC is configured to produce a complete, substantially complete, or even partial nerve block and the other phase is configured (e.g. by reversing the current) to reduce or balance a charge returned to the therapy delivery device. An exemplary multi-phase DC includes relatively slow current ramps that fail to produce an onset response in the neural tissue.

For example, with reference to FIG. 11, illustrated are multi-phase DC waveforms having a substantially trapezoidal delivered by four electrode contacts ("1," "2," "3," and "4") of a therapy delivery device. Each of the cathodic and anodic DC phases begins and ends with a ramp, which prevents or substantially prevents any axonal firing. At the plateau of the cathodic DC phase, for example, there is complete neural block. As discussed above, the cathodic DC phase can cause neural block and, following this phase, the current is reversed (anodic DC phase) to balance the charge delivered by the therapy delivery device. The anodic recharge time can be about equal to, or moderately longer than the cathodic block time. Moreover, the cycles of cathodic block and anodic recharge can be applied to the neural tissue sequentially for prolonged periods of time without any neural damage. Again, the sequence of the DC phases can be reversed and the anodic DC phase may cause the neural block and the cathodic DC phase may balance the charge delivered by the therapy delivery device.

In some instances, the cathodic DC phase is conducted as follows. A DC having a first DC amplitude can be applied to the neural tissue. The first DC is then increased, over a first period of time, to a second DC amplitude. The DC having the first amplitude is insufficient to produce a partial or complete neural block. Next, the second DC amplitude is substantially maintained over a second period of time that is sufficient to produce a complete neural block. After the second period of time, the second DC amplitude is decreased to a third DC amplitude that is equal to, or about equal to, the first DC amplitude.

In some examples, the total net charge delivered by any of the electrode contacts can be equal to, or about equal to zero. Advantageously, delivery of a net zero charge is considerably safer to neural tissue. However, due to external factors that lead to the entire charge not being delivered by the first phase, the waveforms need not be entirely charge balanced, and instead need only be substantially charge balanced.

Application of DC and HFAC

In another example, the ENCB can include a combined delivery of DC and HFAC waveforms to reduce or eliminate an "onset response" (due to the HFAC) without causing electrochemical damage (due to the DC). HFAC has been demonstrated to provide a safe, localized, reversible, electrical neural conduction block. HFAC, however, produces an onset response of short but intense burst of firing at the start of HFAC. Use of short durations of DC to block the neural conduction during this HFAC onset phase can eliminate the onset problem, but DC can produce neural block, it can cause damage to neural tissue within a short period of time. Using a Hi-Q DC electrode contact can reduce or eliminate the damage caused by the DC due to the formation of damaging electrochemical reaction products.

Figure 12:
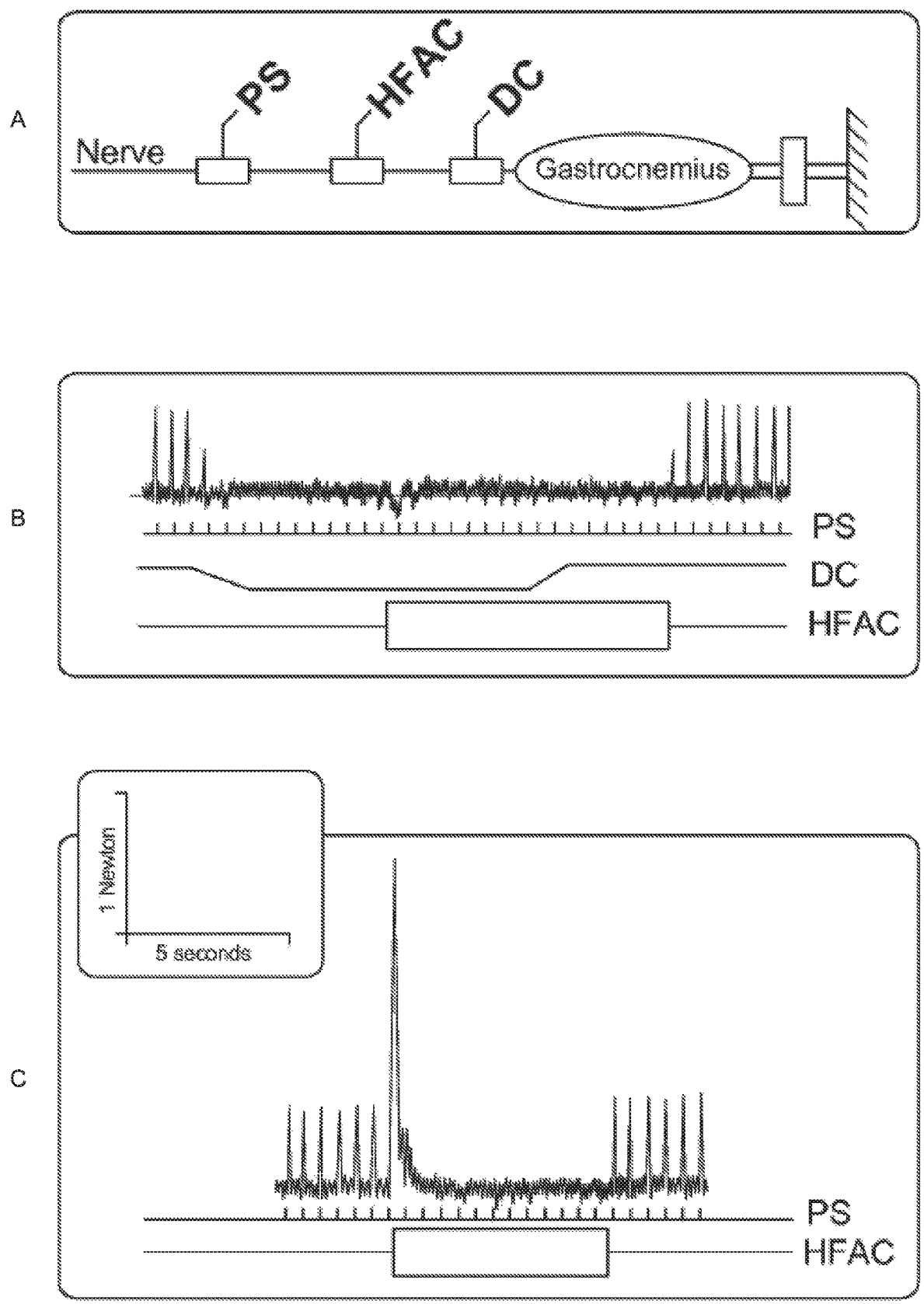
FIG. 12 is an illustration of an experimental setup and an ENCB using a DC plus HFAC no-onset blocking waveform.

Using a combination of a Hi-Q DC electrode contact and a HFAC electrode contact, successful no-onset block was demonstrated, as shown in FIGS. 12 A-C. FIG. 12A shows an example of an experimental setup that can be used to apply DC and HFAC to a nerve. Application of the HFAC alone leads to an onset response, as shown in FIG. 12C. However, when a DC is applied before the HFAC, as shown in FIG. 12B, the block is achieved without the onset response. In experiments with this method, more than fifty successive block sessions without degrading nerve conduction was achieved. DC block (at 2.4 mA) was repeatedly applied over the course of approximately two hours for a cumulative DC delivery of 1500 seconds with no degradation in nerve conduction. FIG. 12B (compared to FIG. 12C) shows the successful elimination of the onset response using the combination of HFAC and Hi-Q DC nerve block.

Figure 13:
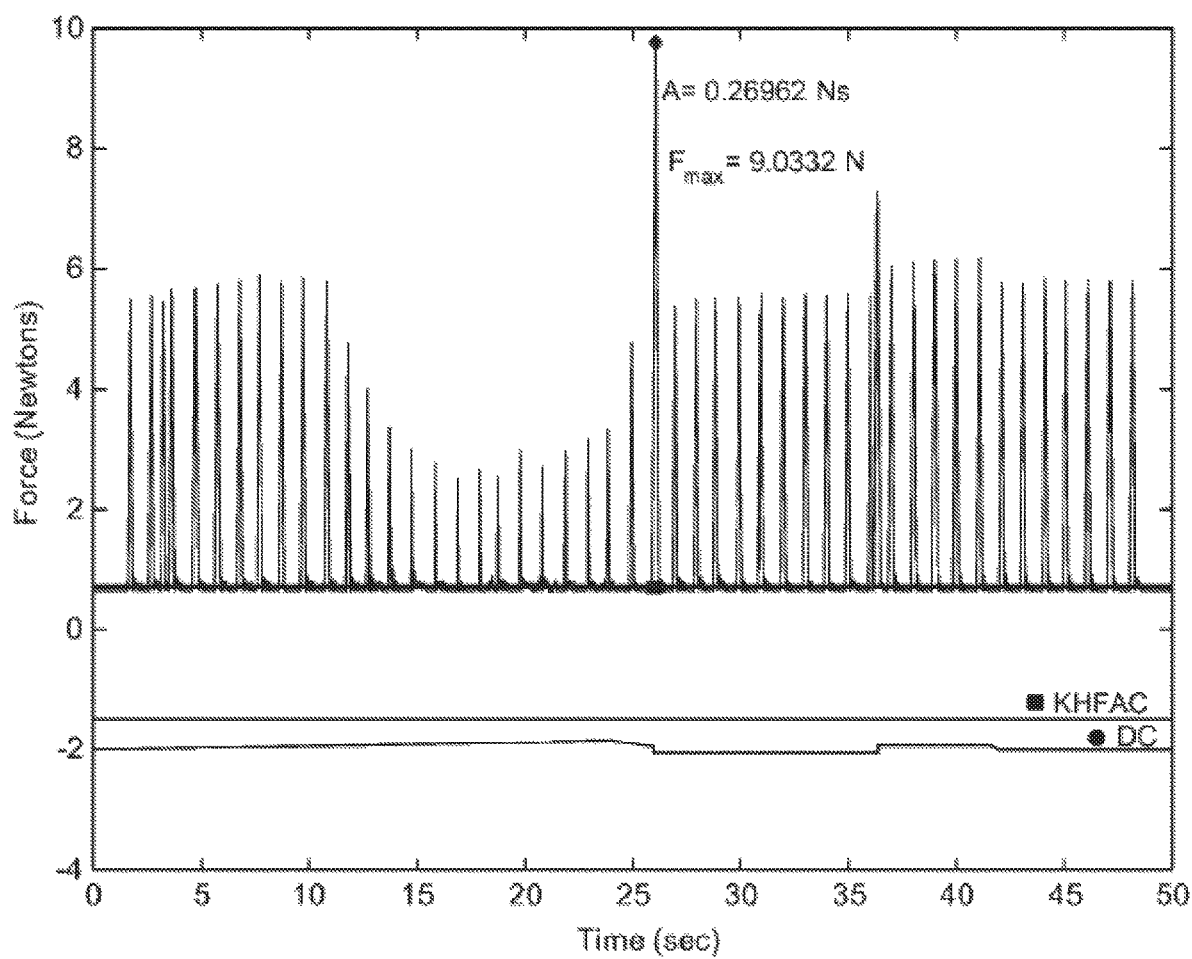
FIG. 13 is an illustration of the DC delivery with a pre-charge pulse, a blocking phase of opposite polarity and a final recharge phase.

One example use of a combined HFAC and Hi-Q DC nerve block allows the DC to be delivered for a period of time sufficient to block the entire onset response of the HFAC. This typically lasts 1 to 10 seconds, and thus the DC should be delivered for that entire period. A method of further extending the total plateau time over which the DC can be safely delivered is to use a "pre-charge" pulse, as shown in FIG. 13. The pre-charge pulse comprises delivering a DC wave of opposite polarity from desired block effect for a length of time up to the maximum charge capacity of the electrode contact. The DC polarity is then reversed to produce the block effect. However, the block can now be delivered longer (e.g., twice as long) because the electrode contact has been "pre-charged" to an opposite polarity. At the end of the prolonged block phase, the polarity is again reversed back to the same polarity as the pre-charge phase, and the total charge is reduced by delivery of this final phase. In most cases, the total net charge of this waveform will be zero, although beneficial effects can be obtained even if the total net charge is not completely balanced.

Figure 14:
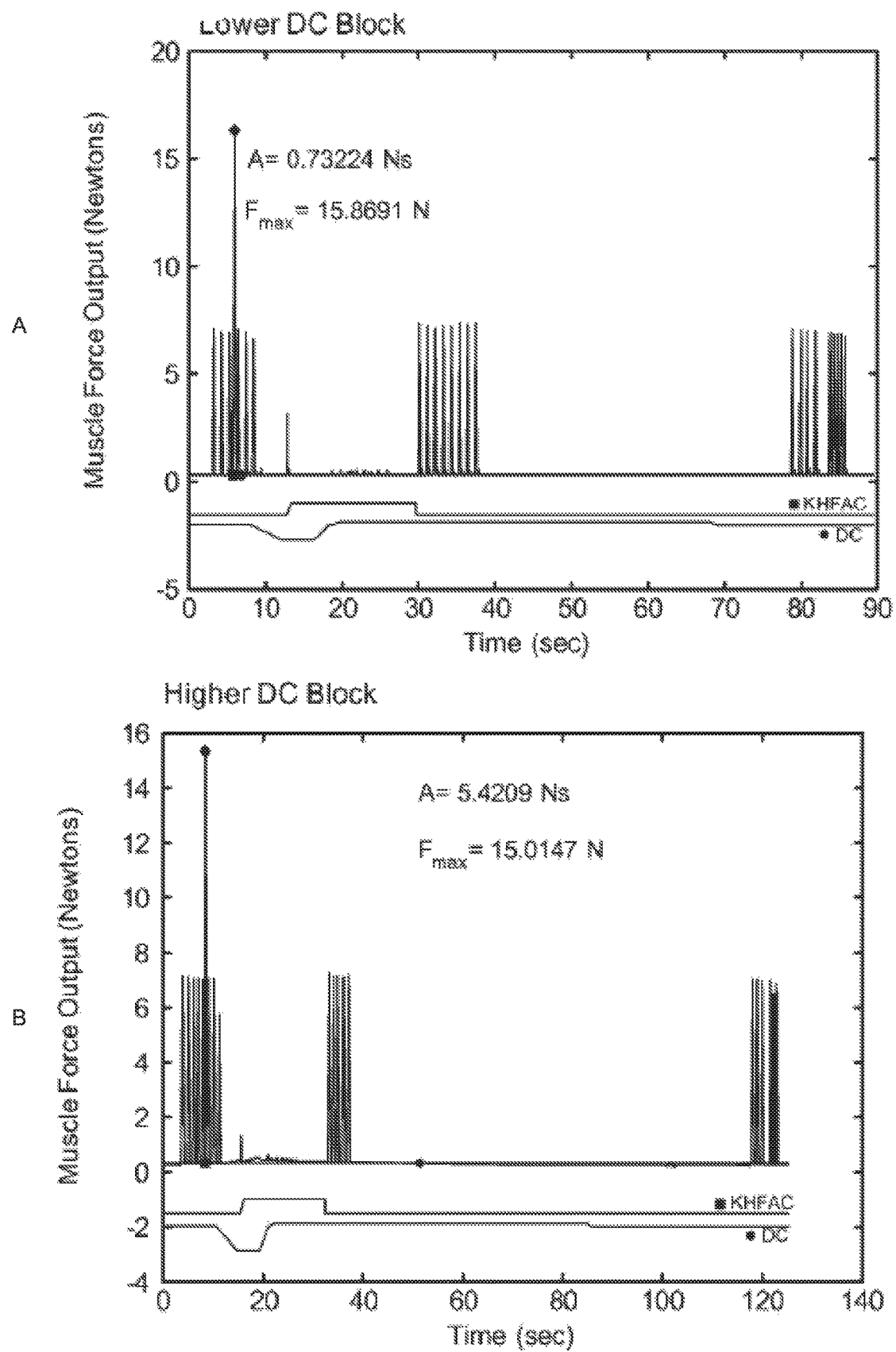
FIG. 14 is an illustration of the effect of electric nerve conduction block waveforms on evoked gastronomies muscle forces, illustrating that different amplitudes of DC block will block different percentages of the HFAC onset response.

Varying the level of DC can partially or fully block the onset response from the HFAC, as shown in FIGS. 14 A-B. FIG. 14A is a graph illustrating that application of HFAC alone results in a large onset response before muscle activity is suppressed. FIG. 14B is graph illustrating that a ramped DC waveform reduces the twitches evoked by PS and minimized the onset response caused by the HFAC waveform. The bar below the "HFAC" indicates when it is turned on. The bar under "DC" indicates when the DC is ramped from zero down to the blocking level and then back to zero again (zero DC is not shown). This can be useful to assess the nerve health by verifying a small response even in the midst of significant nerve block. The depth of the DC block can be assessed through this method.

Figure 15:
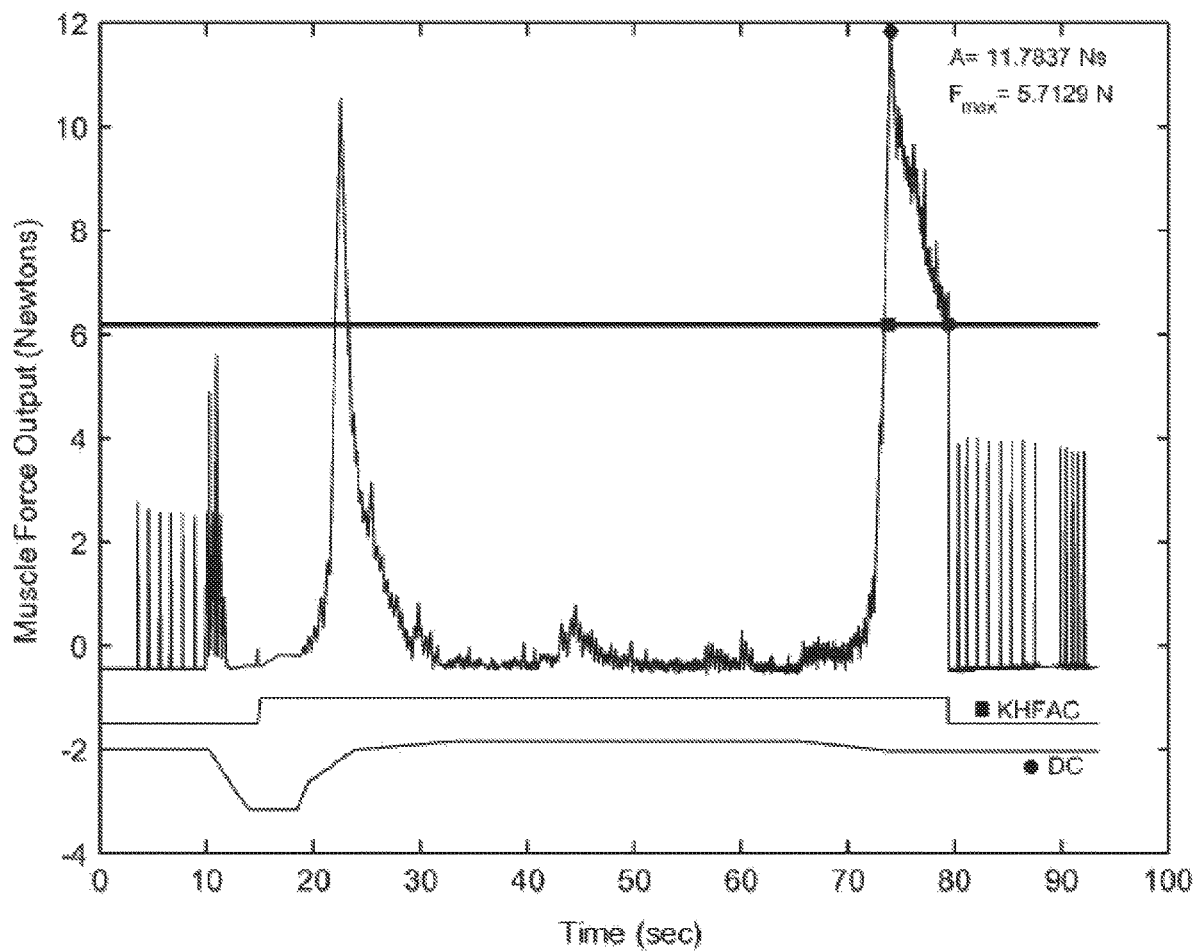
FIGS. 15 and 16 each illustrate the use of different slopes and multiple transitions in the DC waveform to avoid activating a muscle as the current level is varied.
Figure 16:
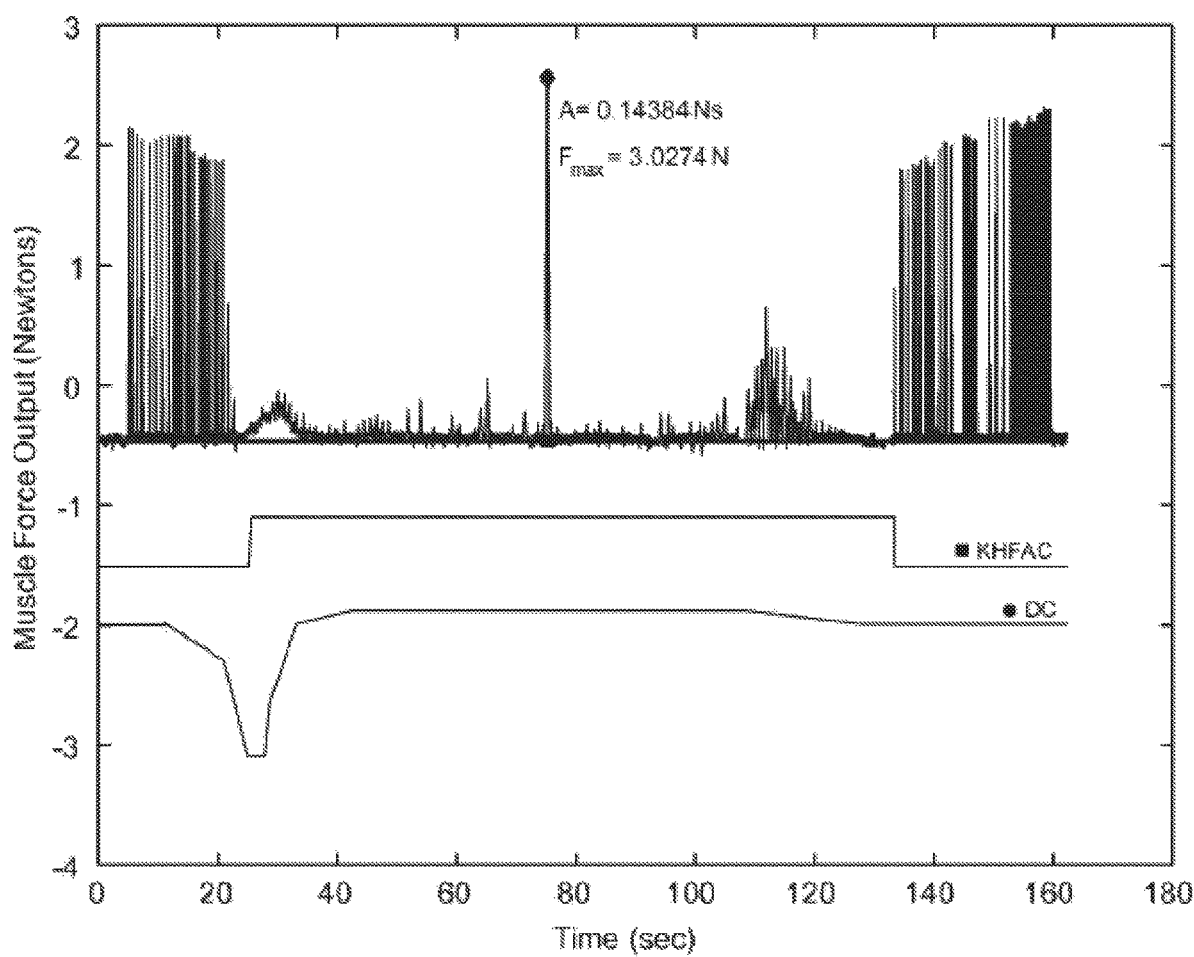

Multi-Slope transitions may help avoid onset response, especially with discrete changes in DC-current-amplitude over time (slope) in a real-world device. This is shown in FIGS. 15 and 16, which are results from a rat's sciatic nerve. In these examples, the DC begins with a low slope to prevent firing of the nerve at low amplitudes. The slope can then be increased to reach the blocking amplitude quicker. Once DC block amplitude has been achieved, block is maintained for the duration required to block the HFAC onset response. The HFAC is turned on once the DC has reached blocking plateau. The HFAC is turned on at the amplitude necessary to block. Once the onset response has completed, the DC is reduced, initially rapidly and then more slowly in order to prevent activation of the nerve. The DC is then slowly transitioned to the recharge phase where the total charge injection is reduced. In this example, the recharge phase is at a low amplitude and lasts for over 100 seconds. HFAC block can be maintained throughout this period and can then be continued beyond the end of the DC delivery if continued nerve block is desired. Once the total period of desired block has been completed (which could be many hours in some cases), the HFAC can be turned off and the nerve allowed to return to normal conducting condition. This process can be repeated again and again as needed to produce nerve block on command as desired to treat disease.

Figure 17:
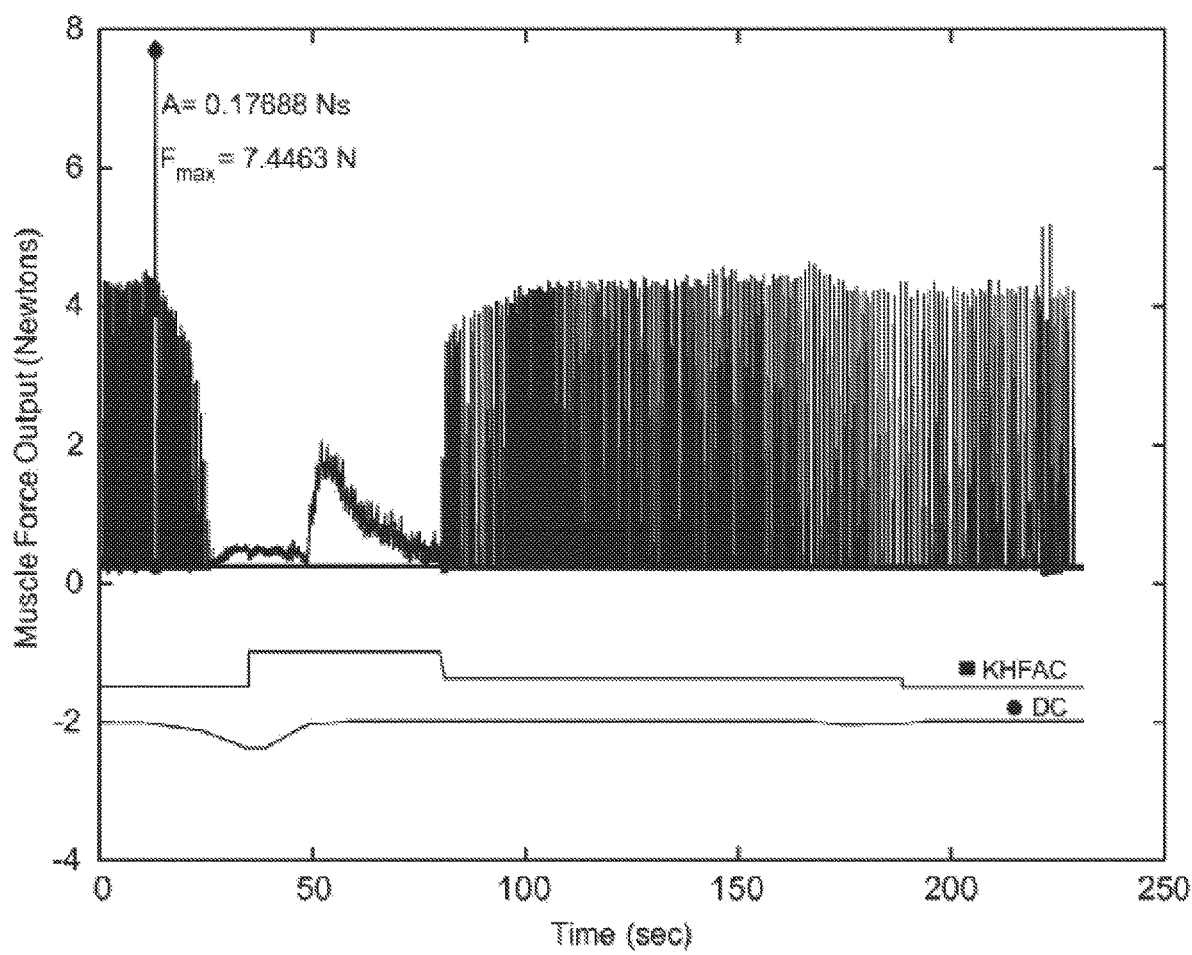
FIG. 17 illustrates a DC block that is too short to block the entire HFAC onset response.

FIG. 17 shows that the DC is maintained throughout the period of the onset response from the HFAC in order to block the entire onset response. In this example (rat sciatic nerve), the onset response lasts about 30 seconds. The DC waveform (blue trace) initially blocks the onset response, but when the DC ramps back to zero, the onset response becomes apparent (at ~50 seconds). This illustrates very long DC blocking waveforms to combine the HFAC and DC blocks to achieve a no-onset block.

VI. Examples—Potential Clinical Applications

The electrode and waveform design described above can be used in many different clinical applications to treat a neurological disorder using ENCB (applied to any peripheral nerve or central nervous system structure) without producing damaging electrochemical reaction products. The ENCB can be reversible, so that when the ENCB is turned off, conduction can be restored in the stimulated nerve.

Figure 18:
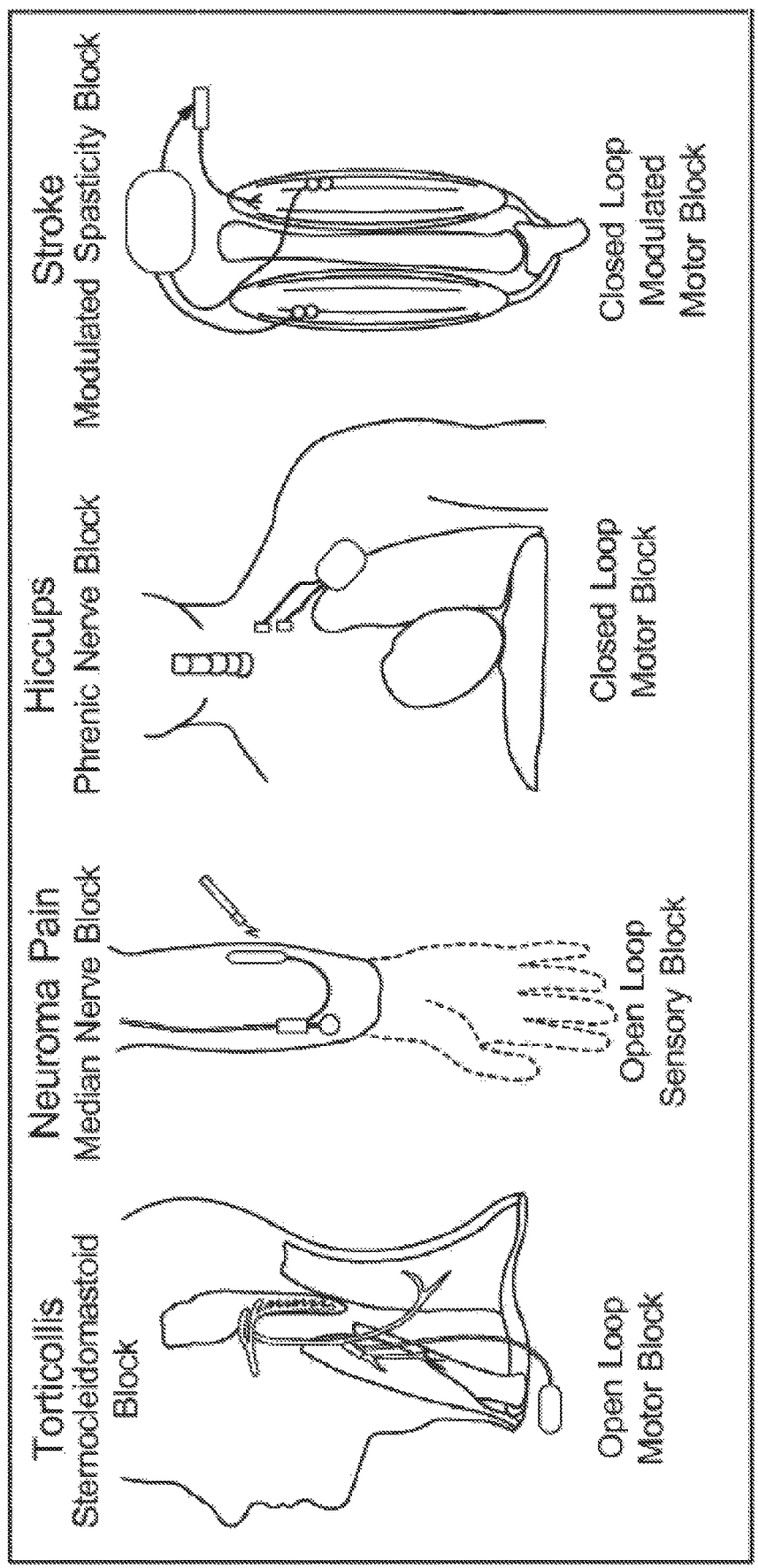
FIG. 18 is a schematic illustration showing non-limiting examples of potential clinical applications for ENCB.

ENCB can be used to treat a number of different neurological disorders in a patient. For example, FIG. 18 shows that different types of ENCB can be applied in different ways to different nerves to treat torticollis (e.g., open loop control), neuroma pain (open loop control), hiccups (e.g., closed loop control), and spasticity/joint contractures (e.g., open loop control or closed loop control). Other example uses of ENCB include treatment of pain (e.g., cancer pain, back pain, joint replacement pain, endometriosis pain, and other types of pain), hyperhidrosis, vertigo, and sialorrhea. Still other examples uses of ENCB include relaxation of the urethral sphincter and mitigating intractable hiccups. Treatment of each of these neurological disorders can be accomplished by applying one or more waveforms (DC and/or HFAC) through an electrode contact (of a cuff electrode, placed beside a nerve, or of an external electrode, for example) without negative side effects by using electrode contacts that include the high charge capacity material, as described above. In addition, in some instances, the ENCB can be combined with other types of nerve block, such as pharmacological block or thermal block (involving heating or cooling of the nerve), to facilitate the treatment of these neurological disorders.

Spasticity

ENCB can be used to reduce or eliminate muscle spasticity or spasms for the purpose of preventing or reversing joint contractures. This is particularly applicable to diseases like cerebral palsy, stroke, and multiple sclerosis, as well as spinal cord injury and post-orthopedic surgery. In each of these cases, muscle spasticity and spasms can be a significant co-morbidity, causing joints to contract and remain contracted when the patient desires to relax. Over time, such contraction can lead to a physiologic shortening of the contracted muscles, causing permanent joint contractures and loss of range of motion in the joint. When these contractures occur, traditional treatments are often destructive and irreversible with often poor outcomes. For example, traditional treatment methods involve damaging nerve fibers, either chemically or surgically, or surgical sectioning of tendons.

In contrast, ENCB, advantageously, can be applied to block spastic signals on motor or sensory nerves, causing the muscles to relax. In some instances, the ENCB can be applied using an open loop control system, where a patient is given a switch or other input device to turn the block on and off and to control the degree of block.

ENCB is reversible, allowing patients to relax the muscles as desired, yet reverse the block when necessary. For example, ENCB can be applied during periods of rest at night or when the individual is less active, allowing the muscles to fully relax, but shut off (reversed) when the individual is active. Since the treatment with ENCB is not destructive, so the treatment can be performed much earlier in the disease progression progress, therefore preventing contractures from occurring.

In some instances, the ENCB can be used to produce a partial nerve block, which can be beneficial with preserving motor function. In a partial block, some, but not all, of the neural signals to the muscle fibers are blocked and the muscle contraction strength is lessened. This can allow voluntary movements of the spastic muscle without triggering the overpowering contraction that is common to spastic muscles. In this case, antagonist muscles can be strong enough to move the joint through the full range of motion.

An example application of ENCB is for prevention/treatment of contractures in spastic cerebral palsy. Spastic ankle plantar flexors and hip adductors in cerebral palsy result in a characteristic pattern of contractures that limit function, make hygiene difficult and can become painful. Release of gastronomies tightness through tendon lengthening or neurolysis is usually only performed as a last resort due to the irreversible nature of these procedures. In some instances, reversible ENCB can be applied to the oburator nerve to relax the hip abductors and to the posterior tibial nerve to block ankle plantarflexion. The ENCB can be applied for many hours throughout the day, with the patient able to turn off the block when movement is desired. Another examples application of ENCB is torticollis, which can be used to treat/prevent involuntary movements and spasticity that occur in conditions such as dystonias, choreas and tics by blocking the sternocleidomastoid muscle and, in some cases, block of the posterior neck muscles.

The ENCB can be accomplished through multiple methods. In some instances, charge balanced or imbalanced HFAC waveforms (voltage controlled or current controlled) can be used to produce a rapidly-induced and rapidly-reversible nerve conduction block. Typical waveform frequencies can be between 5 and 50 kHz. The waveform can be continuous or interrupted, and each pulse can have a varied shape, including square, triangular, sinusoidal, or the like.

In other instances, charge balanced DC waveforms consisting of an increase to a plateau of one polarity, which can last for a time period (e.g., 10 seconds), followed by a decrease of the current to an opposite polarity, can be used for the ENCB. The plateaus of each phase can be the same, but typically the second phase is 10-30% of the amplitude of the first phase. The total charge delivery is zero or substantially less than the charge in each phase (e.g., <10% charge imbalance). The waveform produces either a depolarizing or a hyperpolarizing nerve block during the first phase plateau, and in some cases also blocks during the second phase plateau. Increasing the current from zero to the plateau is often performed slowly over the course of a few seconds in order to eliminate the generation of action potentials in the nerves. Additionally, multiple electrode contacts can be used to maintain a constant conduction block by cycling between the different contacts to deliver the DC waveform to the nerve.

In still other instances, a DC waveform and the HFAC waveform can be combined to produce a nerve block with the desirable characteristics of each type of ENCB. The charge balanced DC can be established first and used to block the onset response from the HFAC, which typically lasts a few seconds. Once the onset response is complete, the charge balanced DC waveform can be terminated (typically after charge balancing) and block can be maintained with the HFAC waveform.

Pain

ENCB can be used to treat both acute and chronic pain due to, for example, cancer, pancreatitis, neuroma, endometriosis, post-herpetic neuralgia, back pain, headache, and joint replacement. In fact, the ENCB can be used to block any nerve conduction leading to the perception of pain as an alternative to neurolysis or chemical block. Notably, ENCB is reversible and can be used early in the treatment because if there are any side effects, they can be alleviated immediately by turning the block off. Additionally, the intensity and extent of the ENCB can be adjustable (e.g., as an open loop system).

Depending on the pain treated with the ENCB, the electrode contacts can be part of a cuff electrode, electrode contacts located near the target nerve, a paddle-style electrode, a mesh-style electrode, or the like. In some instances, the ENCB can be delivered to an autonomic nerve (e.g., the sympathetic ganglia) as an alternative to blocking sensory nerves, which can produce a side effect of a dull buzzing sensation felt due to the stimulation.

The ENCB can be accomplished through multiple methods. In some instances, charge balanced or imbalanced HFAC waveforms (voltage controlled or current controlled) can be used to produce a rapidly-induced and rapidly-reversible nerve conduction block. Typical waveform frequencies can be between 5 and 50 kHz. The waveform can be continuous or interrupted, and each pulse can have a varied shape, including square, triangular, sinusoidal, or the like.

In other instances, charge balanced DC waveforms consisting of an increase to a plateau of one polarity, which can last for a time period (e.g., 10 seconds), followed by a decrease of the current to an opposite polarity, can be used for the ENCB. The plateaus of each phase can be the same, but typically the second phase is 10-30% of the amplitude of the first phase. The total charge delivery is zero or substantially less than the charge in each phase (e.g., <10% charge imbalance). The waveform produces either a depolarizing or a hyperpolarizing nerve block during the first phase plateau, and in some cases also blocks during the second phase plateau. Increasing the current from zero to the plateau is often performed slowly over the course of a few seconds in order to eliminate the generation of action potentials in the nerves. Additionally, multiple electrode contacts can be used to maintain a constant conduction block by cycling between the different contacts to deliver the DC waveform to the nerve.

In still other instances, a DC waveform and the HFAC waveform can be combined to produce a nerve block with the desirable characteristics of each type of ENCB. The charge balanced DC can be established first and used to block the onset response from the HFAC, which typically lasts a few seconds. Once the onset response is complete, the charge balanced DC waveform can be terminated (typically after charge balancing) and block can be maintained with the HFAC waveform.

Relaxation of the Urethral Sphincter

Reversible ENCB can be applied to produce a relaxation of the urinary sphincter on command (e.g., in an open loop system). An example of an application where this is important is in electrical stimulation systems designed to produce bladder evacuation for individuals with spinal cord injury. In these systems, stimulation of the sacral roots produces bladder contraction for evacuation, but also produces unwanted sphincter contraction. The methods of the present disclosure can be applied bilaterally to the pudendal nerve to prevent sphincter activity during bladder activation. After the bladder is emptied, the block can be turned off to restore continence. The blocking electrode contact may also be used as stimulation to activate a weak sphincter and improve continence. Nerve conduction block on the sacral sensory roots can also be used to prevent spontaneous bladder contraction and thus improve continence. Methods can also be used to control bladder-sphincter dyssynergia in spinal cord injury.

Hyperhidrosis

Reversible ENCB can be applied to neural structures of the sympathetic nervous system (e.g., in an open loop system) to treat hyperhidrosis (sweaty palms). The ENCB is a reversible alternative to the traditional sympathectomy, which involves a permanent surgical destruction or disruption of fibers in the sympathetic chain. Sympathectomy is permanent and may have irreversible side effects (like without an excessive reduction leading to dry skin and other side effects associated with destruction of the sympathetic system). In contrast, ENCB can accomplish the same desirable effect without producing any permanent damage to any neural structures. The ENCB can be applied when needed and/or adjusted so to provide a desired degree of reduction in palmar sweating, without the undesirable side effects.

In one example, the ENCB can be applied to specific regions of the sympathetic nervous system. For example, the ENCB can be applied by electrode contacts placed adjacent a targeted sympathetic ganglia so that an electric field generated with sufficient intensity so that the action potentials transmitted within or between sympathetic ganglia are blocked or down-regulated. In other instances, the ENCB can be applied to by nerve cuff electrodes placed around the sympathetic chain (e.g., around sympathetic fibers between ganglia, the sympathetic roots, or the sympathetic ganglia).

The ENCB can be accomplished through multiple methods. In some instances, charge balanced or imbalanced HFAC waveforms (voltage controlled or current controlled) can be used to produce a rapidly-induced and rapidly-reversible nerve conduction block. Typical waveform frequencies can be between 5 and 50 kHz. The waveform can be continuous or interrupted, and each pulse can have a varied shape, including square, triangular, sinusoidal, or the like.

In other instances, charge balanced DC waveforms consisting of an increase to a plateau of one polarity, which can last for a time period (e.g., 10 seconds), followed by a decrease of the current to an opposite polarity, can be used for the ENCB. The plateaus of each phase can be the same, but typically the second phase is 10-30% of the amplitude of the first phase. The total charge delivery is zero or substantially less than the charge in each phase (e.g., <10% charge imbalance). The waveform produces either a depolarizing or a hyperpolarizing nerve block during the first phase plateau, and in some cases also blocks during the second phase plateau. Increasing the current from zero to the plateau is often performed slowly over the course of a few seconds in order to eliminate the generation of action potentials in the nerves. Additionally, multiple electrode contacts can be used to maintain a constant conduction block by cycling between the different contacts to deliver the DC waveform to the nerve.

In still other instances, a DC waveform and the HFAC waveform can be combined to produce a nerve block with the desirable characteristics of each type of ENCB. The charge balanced DC can be established first and used to block the onset response from the HFAC, which typically lasts a few seconds. Once the onset response is complete, the charge balanced DC waveform can be terminated (typically after charge balancing) and block can be maintained with the HFAC waveform.

Vertigo

Reversible ENCB can also be applied to the neural structures of the inner ear to treat vertigo. For example, vertigo can result from Meniere's disease, which is a disorder of the inner ear (that can occur in one or both ears) causing spontaneous vertigo episodes. Traditionally, vertigo can be treated by sectioning the vestibular nerve, which involves identifying the vestibular nerve in the inner ear and cutting the nerve while sparing the cochlear nerve, which runs adjacent to the vestibular nerve. Advantageously, ENCB can be used to produce a similar effect, yet ENCB is fully reversible, which eliminates any permanent side effects, including loss of hearing (which occurs in about 20% of vestibular nerve sections). The ENCB can be applied completely (e.g., controlled as a closed loop by one or more sensors or as an open loop by a physician) and continuously or episodically (e.g., controlled as an open loop by the patient or physician) as needed to one or both ears.

The ENCB can be delivered by electrode contacts placed distally to avoid blocking the cochlear nerve. Alternatively, a nerve cuff electrode can be placed directly around the vestibular nerve branch to deliver the ENCB, which allows for block of the entire vestibular nerve. Insulation around the nerve cuff electrode prevents current spread to the adjacent cochlear nerve, preserving hearing during the block of the vestibular nerve. As another alternative, the nerve cuff electrode can be placed around the entire vestibulocochlear nerve, and the ENCB can be applied to reduce vertigo, but result in significant hearing loss. However, the hearing loss is only temporary since the ENCB is reversible.

The ENCB can be accomplished through multiple methods. In some instances, charge balanced or imbalanced HFAC waveforms (voltage controlled or current controlled) can be used to produce a rapidly-induced and rapidly-reversible nerve conduction block. Typical waveform frequencies can be between 5 and 50 kHz. The waveform can be continuous or interrupted, and each pulse can have a varied shape, including square, triangular, sinusoidal, or the like.

In other instances, charge balanced DC waveforms consisting of an increase to a plateau of one polarity, which can last for a time period (e.g., 10 seconds), followed by a decrease of the current to an opposite polarity, can be used for the ENCB. The plateaus of each phase can be the same, but typically the second phase is 10-30% of the amplitude of the first phase. The total charge delivery is zero or substantially less than the charge in each phase (e.g., <10% charge imbalance). The waveform produces either a depolarizing or a hyperpolarizing nerve block during the first phase plateau, and in some cases also blocks during the second phase plateau. Increasing the current from zero to the plateau is often performed slowly over the course of a few seconds in order to eliminate the generation of action potentials in the nerves. Additionally, multiple electrode contacts can be used to maintain a constant conduction block by cycling between the different contacts to deliver the DC waveform to the nerve.

In still other instances, a DC waveform and the HFAC waveform can be combined to produce a nerve block with the desirable characteristics of each type of ENCB. The charge balanced DC can be established first and used to block the onset response from the HFAC, which typically lasts a few seconds. Once the onset response is complete, the charge balanced DC waveform can be terminated (typically after charge balancing) and block can be maintained with the HFAC waveform.

Sialorrhea

Sialorrhea or excessive drooling is a major issue in children with cerebral palsy and adjust with neurodegenerative disorders. Current medical management, using topical agents, oral agents, and botulinum toxim, is unsatisfactory because these treatments are ineffective or produce unwanted side effects, including lack of salivation when desired. Advantageously, ENCB can be used as an alternative to these traditional treatments that can rapidly and reversibly block activation of the salivary glands, therefore reducing saliva production when desired. The advantages of ENCB include the ability of a patient or caregiver to turn on and of the activation of the salivary glands when desired. Additionally, ENCB can provide for partial or incomplete block, reducing, but not eliminating, salivation, thereby alleviating the symptoms without producing unwanted side effects.

ENCB for alleviation of sialorrhea can be applied to the nerve branches supplying the autonomic activation of the salivary glands, targeting one or more nerves. Alternatively, linear electrodes with one or more contacts can be placed adjacent to the target nerves to produce the desired block. This approach may simplify surgical installation. ENCB may be applied directly to or near each salivary gland.

The ENCB can be accomplished through multiple methods. In some instances, charge balanced or imbalanced HFAC waveforms (voltage controlled or current controlled) can be used to produce a rapidly-induced and rapidly-reversible nerve conduction block. Typical waveform frequencies can be between 5 and 50 kHz. The waveform can be continuous or interrupted, and each pulse can have a varied shape, including square, triangular, sinusoidal, or the like.

In other instances, charge balanced DC waveforms consisting of an increase to a plateau of one polarity, which can last for a time period (e.g., 10 seconds), followed by a decrease of the current to an opposite polarity, can be used for the ENCB. The plateaus of each phase can be the same, but typically the second phase is 10-30% of the amplitude of the first phase. The total charge delivery is zero or substantially less than the charge in each phase (e.g., <10% charge imbalance). The waveform produces either a depolarizing or a hyperpolarizing nerve block during the first phase plateau, and in some cases also blocks during the second phase plateau. Increasing the current from zero to the plateau is often performed slowly over the course of a few seconds in order to eliminate the generation of action potentials in the nerves. Additionally, multiple electrode contacts can be used to maintain a constant conduction block by cycling between the different contacts to deliver the DC waveform to the nerve.

In still other instances, a DC waveform and the HFAC waveform can be combined to produce a nerve block with the desirable characteristics of each type of ENCB. The charge balanced DC can be established first and used to block the onset response from the HFAC, which typically lasts a few seconds. Once the onset response is complete, the charge balanced DC waveform can be terminated (typically after charge balancing) and block can be maintained with the HFAC waveform.

Intractable Hiccups

ENCB can be used to mitigate intractable hiccups where by blocking phrenic nerve conduction. For example, an impending hiccup can be sensed through a nerve signal recording on the proximal phrenic nerve. A large volley of activity, indicating an impending hiccup, can be used to trigger the ENCB more distally on the phrenic nerve. In certain embodiments, the block is only applied for a very brief period in order to block the hiccup, and thus not interfering with normal breathing. The ENCB can include, for example, a DC waveform (through an electrode contact of a high intensity material) followed by an HFAC waveform.

The foregoing description and examples have been set forth merely to illustrate the invention and are not intended as being limiting. For example, ENCB can be used to treat other disorders, such as complications of asthma (opening closed airways) or Parkinson's disease. Each of the disclosed aspects and embodiments of the present disclosure may be considered individually or in combination with other aspects, embodiments, and variations of the disclosure. Further, while certain features of embodiments of the present disclosure may be shown in only certain figures, such features can be incorporated into other embodiments shown in other figures while remaining within the scope of the present disclosure. In addition, unless otherwise specified, none of the steps of the methods of the present invention are confined to any particular order of performance Modifications of the disclosed embodiments incorporating the spirit and substance of the disclosure may occur to persons skilled in the art and such modifications are within the scope of the present disclosure. Furthermore, all references cited herein are incorporated by reference in their entirety.

What is claimed is:

1. A system comprising:
   a waveform generator to generate an electrical nerve conduction block (ENCB);
   a controller coupled with the waveform generator, wherein the controller is configured to receive an input comprising at least one parameter to adjust the ENCB;
   an electrical contact coupled with the waveform generator, wherein the electrical contact is configured to be placed into contact with a nerve, wherein the electrical contact comprises a high charge capacity material that prevents formation of damaging electro-chemical products at a charge delivered by the ENCB;
   wherein the electrical contact is configured to deliver the ENCB to the nerve to block transmission of a signal related to a pain through the nerve.

2. A system according to claim 1, wherein the controller forms part of an open loop control system.

3. A system according to claim 2, wherein the controller is configured to receive the input to adjust the ENCB from a user.

4. A system according to claim 1, wherein the controller forms part of a closed loop control system.

5. A system according to claim 4, wherein the controller is configured to receive the input to adjust the ENCB from an entity.

6. A system according to claim 5, wherein the entity comprises a sensor configured to sense a change in a physiological parameter.

7. A system according to claim 2, wherein the controller is configured to interpret the input and configured to signal the waveform generator including a parameter adjusted based on the input.

8. A system according to claim 7, wherein the waveform generator is configured to generate an appropriate ENCB to be delivered to the nerve based on the adjusted parameter from the controller.

9. A system according to claim 1, wherein, based on the input, the controller is configured to specify a timing parameter, an intensity parameter, a waveform parameter so that an appropriate ENCB is generated.

10. A system according to claim 1, wherein the ENCB comprises at least one of a monophasic direct current (DC) waveform, a charge balanced direct current (CBDC) waveform, a substantially CBDC waveform, and a high frequency alternating current (HFAC) waveform.

11. A system according to claim 1, wherein the waveform generator is configured to generate reversible ENCB so that when transmission of the ENCB is stopped, normal signal transmission through the nerve is restored.

* * * * *